United States Patent
Wong et al.

(10) Patent No.: US 10,307,470 B2
(45) Date of Patent: Jun. 4, 2019

(54) ANTIBODY-MEDIATED ANTI-TUMOR ACTIVITY INDUCED BY REISHI MUSHROOM POLYSACCHARIDES

(71) Applicants: ACADEMIA SINICA, Taipei (TW); Chi-Huey Wong, La Jolla, CA (US); Chung-Yi Wu, New Taipei (TW); Hsien-Yeh Hsu, Taipei (TW); Shih-Fen Liao, Taipei (TW); Chi-Hui Liang, Taipei (TW)

(72) Inventors: Chi-Huey Wong, La Jolla, CA (US); Chung-Yi Wu, New Taipei (TW); Hsien-Yeh Hsu, Taipei (TW); Shih-Fen Liao, Taipei (TW); Chi-Hui Liang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 246 days.

(21) Appl. No.: 14/906,663

(22) PCT Filed: Jul. 26, 2014

(86) PCT No.: PCT/US2014/048325
§ 371 (c)(1),
(2) Date: Jan. 24, 2016

(87) PCT Pub. No.: WO2015/026484
PCT Pub. Date: Feb. 26, 2015

(65) Prior Publication Data
US 2016/0166661 A1 Jun. 16, 2016

Related U.S. Application Data

(60) Provisional application No. 61/859,162, filed on Jul. 26, 2013.

(51) Int. Cl.
*A61K 39/00* (2006.01)
*A61K 36/074* (2006.01)

(52) U.S. Cl.
CPC ........ *A61K 39/0002* (2013.01); *A61K 36/074* (2013.01); *A61K 39/0011* (2013.01); *A61K 2039/55572* (2013.01); *A61K 2039/575* (2013.01)

(58) Field of Classification Search
CPC .............. A61K 39/0002; A61K 36/074; A61K 39/0011; A61K 2039/55572; A61K 2039/575
USPC ....................................................... 424/274.1
See application file for complete search history.

(56) References Cited

U.S. PATENT DOCUMENTS 7,135,183 B1 * 11/2006 Wang .................... A23L 33/105
424/195.15
7,560,114 B2 * 7/2009 Wang .................... A61K 36/074
424/195.15

OTHER PUBLICATIONS

Wang, Y.-Y., et al., Bioorganic & Medicinal Chemistry 10: 1057-1062, 2002.*
Boh, B., Recent Patents of Anti-Cancer Drug Discovery, 8: 255-287, Sep. 2013.*
Lai, C.-Y., et al. Vaccine, 28: 4945-4954, 2010.*

* cited by examiner

*Primary Examiner* — Yih-Horng Shiao
(74) *Attorney, Agent, or Firm* — Birch, Stewart, Kolasch & Birch, LLP

(57) ABSTRACT

Immunogenic compositions, cancer vaccines and methods for treating cancer comprising FMS, the fucose-enriched polysaccharide fraction from Reishi F3, are provided. Compositions comprise fucose-enriched Reishi polysaccharide fraction (FMS) MW=~35 kDa, wherein the FMS is isolated by size-exclusion chromatography from Reishi F3, and the FMS comprises polysaccharides having primarily a backbone selected from 1,4-mannan and 1,6-α-galactan, wherein the backbone is linked to a terminal fucose-containing side-chain Immunogenic compositions comprising glycolipid adjuvants are provided. Antibodies generated by immunogenic compositions disclosed herein bind cancer cells comprising antigens Globo H, Globo H, Gb3, Gb4, Gb5 (SSEA-3) and SSEA-4 on the cell surface.

39 Claims, 11 Drawing Sheets

ANTIBODY-MEDIATED ANTI-TUMOR ACTIVITY INDUCED BY REISHI MUSHROOM POLYSACCHARIDES

CROSS-REFERENCE TO RELATED APPLICATIONS

This application is the US national stage application from international application no. PCT/US2014/048325 filed Jul. 26, 2014 (and published as WO 2015/026484 A1 on 26 Feb. 2015), which claims priority of U.S. provisional patent application Ser. No. 61/859,162, titled "ANTIBODY-MEDIATED ANTI-TUMOR ACTIVITY INDUCED BY REISHI MUSHROOM POLYSACCHARIDES" filed Jul. 26, 2013, both of which are incorporated herein by reference.

TECHNICAL FIELD OF THE INVENTION

This invention relates to the field of cancer vaccines. In particular, the application relates to carbohydrate-based immunogenic compositions containing fucose-enriched polysaccharides isolated from a fucose-containing extract of *Ganoderma lucidum*. More particularly, the invention is directed at cancer vaccines directed at cells containing Globo H and related antigens.

BACKGROUND OF THE INVENTION

Various forms of herbal medicine polysaccharides have become valuable as health supplements worldwide (1, 2), suggesting that administration of such polysaccharides may improve innate immunity in vivo. The underlying molecular mechanisms, however, still remain ambiguous.

To design therapy against cancer, it is desirable to seek molecular targets of cancer or cancer stem cells that are absent from normal cells. Aberrant glycosylation is often associated with tumor progression and was first described by Meezan et al. in 1969 with the demonstration that cancer glycans differ from healthy cells. (Meezan E, et al. (1969) Biochemistry 8:2518-2524.) Aberrant terminal fucosylation as well as sialylation in tumor-associated glycans is one of several glycosylation events important in cancer progression (3, 4), and such unusual glycans have recently been used for the development of anti-cancer vaccines (5-7). Aberrant glycosylations include loss or over-expression of certain structures, the persistence of truncated structures and the emergence of novel structures. The structural differences were later supported by many histological evidences using lectin-staining compared with healthy and malignant tissue. (Turner G A (1992) Clin Chim Acta 208:149-171; Gabius H J (2000) Naturwissenschaften 87:108-121.)

More recently, tumor associated carbohydrate antigens were identified by monoclonal antibodies and mass spectrometry. (Shriver Z, et al. (2004) Nat Rev Drug Disc 3:863-873; Pacino G, et al. (1991) Br J Cancer 63:390-398.) To date, numerous tumor associated antigens expressed on cancer cells in the form of glycolipids or glycoproteins have been characterized and correlated to certain types of cancers. (Bertozzi C R, Dube D H (2005) Nat Rev Drug Discovery 4:477-488.) Although relatively little is known about the role of surface carbohydrates play in malignant cells, passively administered or vaccine induced antibodies against these antigens have correlated with improved prognosis.

Of the tumor associated glycans reported, the glycolipid antigen Globo H (Fucα1→2 Galβ1→3 GalNAcβ1→3 Galα1→4 Galβ1→4 Glc) was first isolated and identified in 1984 by Hakomori et al. from breast cancer MCF-7 cells. (Bremer E G, et al. (1984) J Biol Chem 259:14773-14777.) Further studies with anti-Globo H monoclonal antibodies showed that Globo H was present on many other cancers, including prostate, gastric, pancreatic, lung, ovarian and colon cancers and only minimal expression on luminal surface of normal secretory tissue which is not readily accessible to immune system. (Ragupathi G, et al. (1997) Angew Chem Int Ed 36:125-128.) In addition, it has been established that the serum of breast cancer patient contains high level of anti-Globo H antibody. (Gilewski T et al. (2001) Proc Natl Acad Sci USA 98:3270-3275; Huang C-Y, et al. (2006) Proc Natl Acad Sci USA 103:15-20; Wang C-C, et al. (2008) Proc Natl Acad Sci USA 105(33):11661-11666) and patients with Globo H-positive tumors showed a shorter survival in comparison to patients with Globo H-negative tumors. (Chang, Y-J, et al. (2007) Proc Natl Acad Sci USA 104(25):10299-10304.) These findings render Globo H, a hexasaccharide epitope, an attractive tumor marker and a feasible target for cancer vaccine development.

As an example, the Globo H-based glycoconjugate vaccines are currently undergoing large-scale clinical trials and have shown promise in therapeutic treatment (8, 9). Studies on the immune response to pathogenic microorganisms (such as *Haemophilus* influenza type B and *Streptococcus pneumonia*) have demonstrated that polysaccharides containing repeating antigenic units are generally T cell-independent (TI) (10, 11).

Globo H is a cancer antigen overly expressed in various epithelial cancers. It has been suggested that this antigen can serve as a target in cancer immunotherapy. While vaccines have been developed to elicit antibody responses against Globo H, their anti-cancer efficacies are unsatisfactory due to low antigenicity of Globo H.

In breast cancer, Globo H expression was observed in >60% of ductal, lobular, and tubular carcinoma, but not in nonepithelial breast tumors (Mariani-Constantini R et al., (1984) Am. J. Pathol. 115:47-56). Globo H is not expressed in normal tissue except for weak expression in the apical epithelial cells at lumen borders, a site that appears to be inaccessible to the immune system (Id.; Zhang S. et al., (1997) Int. J. Cancer 73:42-49).

Globo H also is expressed in breast cancer stem cells (BCSCs). Flow cytometry revealed Globo H is expressed in 25/41 breast cancer specimens (61.0%). Non-BCSCs from 25/25 and BCSCs from 8/40 (20%) express Globo H. The stage-specific embryonic antigen 3 (SSEA-3), the pentasaccharide precursor of Globo H, is expressed in 31/40 (77.5%) tumors. Non-BCSCs from 29/31 and BCSCs from 25/40 (62.5%) expressed SSEA-3. (Chang W-W. et al., (2008) Proc Natl Acad Sci USA 105(33):11667-11672.)

There is a need for a new vaccine capable of eliciting high levels of immune responses targeting Globo H and related antigens.

SUMMARY OF THE INVENTION

This invention relates to a carbohydrate based immunogenic composition containing a fucose-enriched Reishi polysaccharide fraction (FMS) of average molecular weight 35 kDa, wherein the FMS is isolated from Reishi F3, and wherein the FMS comprises polysaccharides having primarily a backbone selected from 1,4-mannan and 1,6-α-galactan, wherein the backbone is linked to a terminal fucose-containing side-chain; and optionally, an adjuvant. In one embodiment, the FMS is isolated by size-exclusion chromatography.

In some embodiments, the adjuvant is a glycolipid. In particular embodiments the adjuvant is a synthetic analog of α-GalCer selected from: 7DW8-5 and C34.

In some embodiments of the method, the immunogenic composition further comprises a cancer vaccine, and further wherein one or more treatments with an effective amount of the cancer vaccine inhibit tumor growth. In some embodiments, administration of the cancer vaccine reduces the size of a tumor.

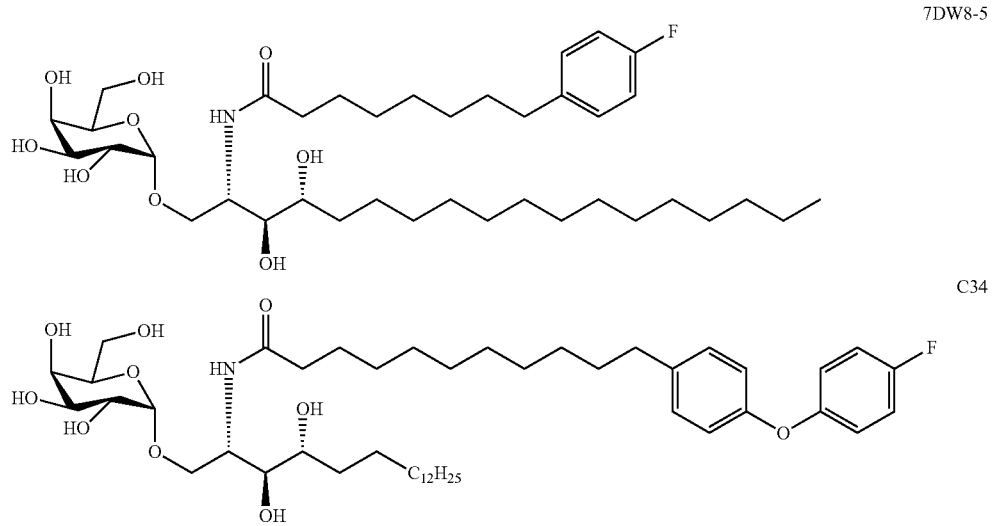

7DW8-5

C34

In one aspect the FMS comprises a backbone is linked to a terminal fucose-containing side-chain through one or more linkages selected from Fucα1-2Gal, Fucα1-3/4Man, Fucα1-4Xyl and Fucα1-2Fuc. The FMS comprises primarily of fucose, xylose, galactose and mannose in the ratio of 2:1.5:2.5:3.5. In some embodiments, the FMS comprises small amounts of glucose, glucosamine and galactosamine.

In one aspect the immunogenic composition in combination with a glycolipid adjuvant induce IgG, IgG1 and IgM antibodies and provide exceptional immunogenicity.

In one aspect, antibodies generated by the immune response specifically bind to at least one of the tumor-associated antigens selected from the group consisting of Globo H, Gb3, Gb4, stage-specific embryonic antigen-3 (SSEA-3; Gb-5; Galβ1-3GalNAcβ1-3Galα1-4Galβ1-4Glcβ)) and SSEA-4 (Neu5Acα2-3Galβ1-3GalNAcβ1-3Galα1-4Galβ1-4Glcβ). all specific for cancer cells.

In some embodiments, the antibodies generated by the immune response specifically bind to a glycan antigen comprising a common structure: Fucα1-2Galβ1-3GalNAc-R in the non-reducing termini.

In one aspect, antibodies generated by the immune response specifically bind to an antigen further comprising an additional disaccharide extension in the reducing end of Fucα1-2Galβ1-3GalNAc-R, wherein the disaccharide moiety is selected from: Fucα1-2Gal-R; Fucα1-3/4Man-R; Fucα1-4Xyl-R and Fucα1-2Fuc-R.

In one aspect, antibodies generated by the immune response specifically bind to α-L-fucose-specific lectin, UEA-I (*Ulex europaeus* agglutinin-I).

In one aspect, antibodies generated by the immune response specifically bind to a glycan antigen comprising s blood group ABH determinant.

In one aspect, antibodies generated by the immune response trigger complement-dependent cytotoxicity (CDC) in a cancer cell. In some embodiments, the CDC activity is sufficient to reduce tumor size in lung cancer cells.

In one aspect, administration of the immunogenic composition results in decrease of serum levels of monocyte chemoattractant protein-1 (MCP-1).

The invention relates to a cancer vaccine comprising a sufficient amount of the immunogenic composition which is able to induce anti-cancer immune responses in a subject. In some aspects, the cancer vaccine is suitable for treating a cancer selected from the group consisting of: breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

The invention further provides methods for use of the aforementioned immunogenic compositions. The invention relates to a method of treatment comprising inhibition of tumor growth, the method comprising: (a) administering to a subject in need thereof, an immunogenic composition comprising: a fucose-enriched Reishi polysaccharide fraction (FMS) of average molecular weight 35 kDa, wherein the FMS is isolated by size-exclusion chromatography from Reishi F3, and wherein the FMS comprises polysaccharides having primarily a backbone selected from 1,4-mannan and 1,6-α-galactan, wherein the backbone is linked to a terminal fucose-containing side-chain; and optionally, an adjuvant; and (b) inducing an immune response that causes inhibition of tumor growth.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

TABLE 1

Compositional assignments of multiple charged sodiated molecular ions observed in nanoLC-MS spectra of permethylated FMS hydrolysate alditols

| Peak | Retention time(min) | Observed m/z[a] | Charge[b] | Sugar composition[c] | Relative intensity[d] |
|---|---|---|---|---|---|
| 1 | 14 | 419.2249 | 1 | P1F1 | 50.9 |
|   |    | 433.2402 | 1 | F2 | 29.2 |
|   |    | 449.2351 | 1 | P1H1 | 58.4 |
|   |    | 463.2505 | 1 | F1H1 | 21.4 |
|   |    | 477.2304 | 1 | F1A1 | 7.2 |
|   |    | 493.2613 | 1 | H2 | 100 |
|   |    | 507.2404 | 1 | A1H1 | 18.4 |
| 2 | 14.2 | 433.2403 | 1 | F2 | 100 |
|   |    | 463.2508 | 1 | F1H1 | 32.1 |
|   |    | 477.2304 | 1 | F1A1 | 8.5 |
|   |    | 493.2614 | 1 | H2 | 54.8 |
|   |    | 507.2406 | 1 | A1H1 | 7 |
| 3 | 14.8 | 697.3604 | 1 | H3 | 100 |
| 4 | 15.7 | 653.3346 | 1 | P1H1 | 100 |
|   |    | 697.3607 | 1 | H3 | 15.6 |
| 5 | 16 | 462.2248 | 2 | H4 | 74.7 |
|   |    | 697.3604 | 1 | H3 | 79.7 |
|   |    | 901.4602 | 1 | H4 | 100 |
| 6 | 17.2 | 564.2745 | 2 | H5 | 100 |
|   |    | 887.4444 | 1 | H4-ol | 5.8 |
|   |    | 1105.5594 | 1 | H5 | 25.3 |
| 7 | 17.6 | 711.34 | 1 | A1H2 | 100 |
| 8 | 17.9 | 813.4088 | 1 | P2H2 | 100 |
| 9 | 18.1 | 440.2121 | 2 | P1H3 | 58.6 |
|   |    | 857.4349 | 1 | P1H3 | 100 |
| 10 | 18.2 | 666.3252 | 2 | H6 | 100 |
|   |    | 1091.545 | 1 | H5-ol | 5 |
|   |    | 1309.6608 | 1 | H6 | 5.3 |
| 11 | 18.9 | 462.2253 | 2 | H4 | 88 |
|   |    | 901.461 | 1 | H4 | 100 |
| 12 | 19.1 | 768.3752 | 2 | H7 | 100 |
|   |    | 1091.5453 | 1 | H5-ol | 3.2 |
|   |    | 1295.6452 | 1 | H6-ol | 2.5 |
| 13 | 20 | 520.2492 | 2 | P2H3 | 25 |
|   |    | 870.4251 | 2 | H8 | 100 |
|   |    | 1017.5083 | 1 | P2H3 | 27.9 |
| 14 | 20.5 | 542.262 | 2 | P1H4 | 100 |
|   |    | 1061.5343 | 1 | P1H4 | 28.8 |
| 15 | 20.7 | 655.9796 | 3 | H9 | 29.6 |
|   |    | 972.4744 | 2 | H9 | 100 |
| 16 | 21.1 | 564.2756 | 2 | H5 | 100 |
|   |    | 666.3246 | 2 | H6 | 21.9 |
|   |    | 887.4461 | 1 | H4-ol | 13.3 |
|   |    | 1105.5615 | 1 | 2 | 17.5 |
| 17 | 21.3 | 724.0137 | 3 | H10 | 71.9 |
|   |    | 1074.5252 | 2 | H10 | 100 |
| 18 | 21.6 | 600.2859 | 2 | P3H3 | 100 |
|   |    | 1177.5817 | 1 | P3H3 | 22.1 |
| 19 | 21.8 | 792.0467 | 3 | H11 | 100 |
|   |    | 1176.5743 | 2 | H11 | 61 |
| 20 | 22 | 622.2997 | 2 | P2H4 | 100 |
|   |    | 1047.5204 | 1 | P1H4-ol | 9.2 |
|   |    | 1221.6095 | 1 | P2H4 | 16.2 |

[a]All observed molecular ions have mass errors below 2 ppm.
[b]Charge state of sodiated molecular ions.
[c]P = pentose; F = fucose; A = hexuronic acid; H = hexose; -ol = neutral loss of a terminal residue.
[d]Relative intensities observe in mass spectrum by average the full width at half maximum of peak.

Figure 11:
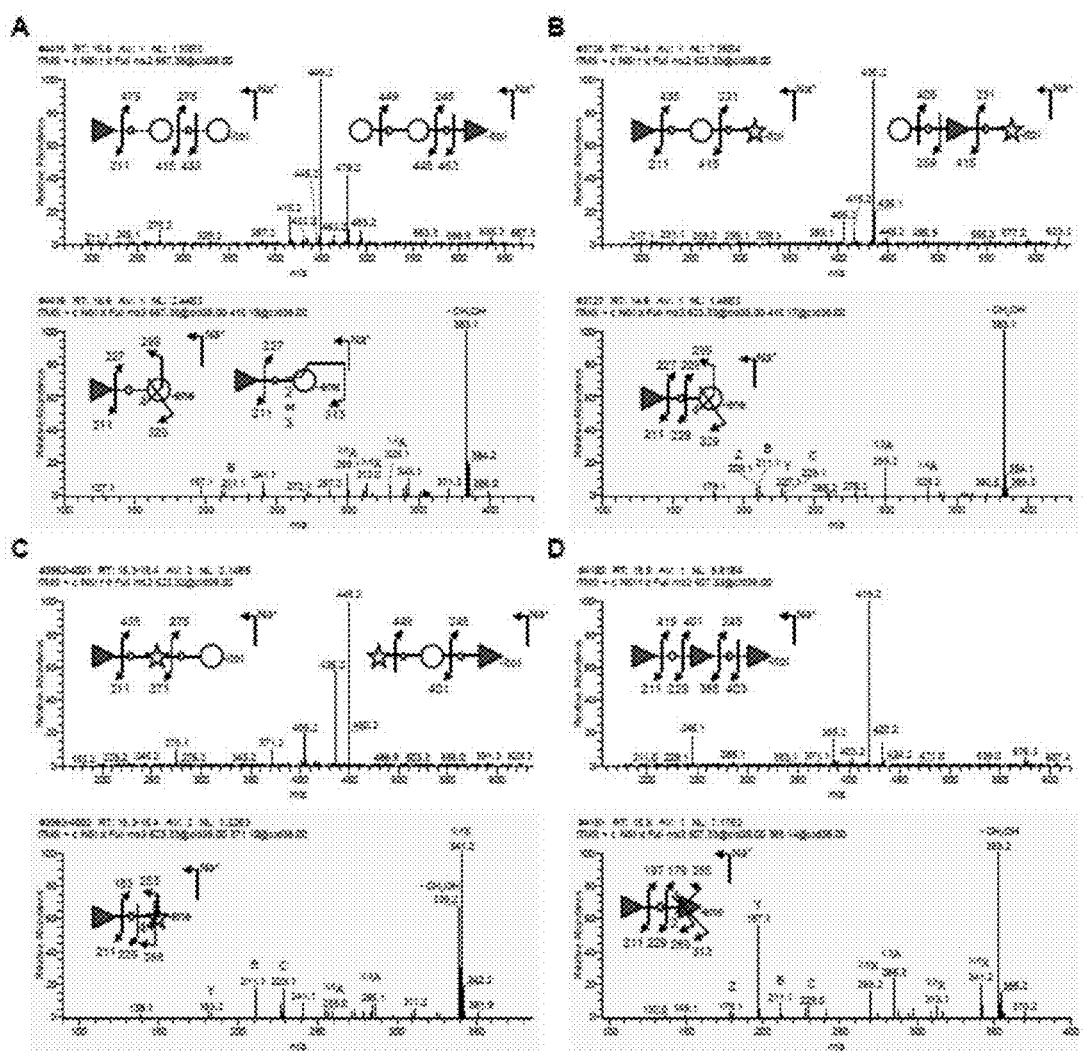

FIG. 11. Targeted nanoLC-MS/MS glycan sequencing and fucosylated epitope linkage determination of permethylated alditols of FMS hydrolysate. The fucosylated glycotope linkages of permethylated FMS hydrolysate alditols were determined by data-dependent MS[2] and following MS[3] (in color background) spectra of (11A) 1Fuc-2Hex-itol, (11B and 11C) 1Fuc-1Xyl-1Hex-itol and (11D) 3Fuc-itol. Red triangle represents fucose residue. White circle represents hexose residue. Asterisk represents xylose residue.

DETAILED DESCRIPTION OF THE INVENTION

"Reishi" means the name for one form of the mushroom *Ganoderma lucidum*, and its close relative *Ganoderma tsugae*. "Purified Reishi" means a reishi extract prepared as described in U.S. Nonprovisional application Ser. No. 11/553,402 and/or Ser. No. 10/213,257 (now U.S. Pat. No. 7,135,183), incorporated by reference herein, wherein the purified reishi is comprised of a polysaccharide or glycopeptide containing terminal fucose residues.

An alkaline extract of Reishi is subjected to size-exclusion chromatography. The main fraction having a light absorbance of about 1.8 at O.D. 625 was designated as Fraction 3. Fraction 3 includes a fucose-containing glycoprotein fraction, which comprises terminal fucose residues. The phrase "terminal fucose residues" identifies fucose residues of a chain of sugars located in a region proximate to a free end of a chain of sugars. The fucose-containing glycoprotein fraction of Fraction 3, also includes fucose residues bound with α1,2-fucosidic linkages and α3,4-fucosidic linkages.

FMS, the fucose-enriched polysaccharide fraction from F3, exhibits unique immunogenicity, and that the mice immunized with F3 or FMS could exert effective antibody-mediated reaction against Globo H-expressing murine LLC1 cells. These findings are consistent with previous assertions that the host immune function enhanced by Reishi polysaccharides offer great promise for the immunotherapy of Globo H-positive lung cancer patients (48). Based on our glycan structural analysis, the most likely fucosyl glycan moieties are Fucα1-2Gal-R; Fucα1-3/4Man-R; Fucα1-4Xyl-R and Fucα1-2Fuc-R.

Some of them activate the antibody responses against tumor-specific glycan epitopes, paving the way for developing complex carbohydrates for immunomodulation-based therapy. Although this study is limited to Reishi polysaccharides and mostly to lung cancer, the approach of high-throughput glycan microarray analysis and detailed structural analyses of carbohydrate antigens should be applicable to other medicinal polysaccharides, which induce different antibody-mediated biological functions.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lanes (Cold Spring Harbor Laboratory Press, 1988); and Handbook Of Experimental Immunology, Volumes I-IV (D. M. Weir and C. C. Blackwell, eds., 1986).

As used herein and in the appended claims, the singular forms "a," "and," and "the" include plural referents unless the context clearly dictates otherwise. Thus, for example, "a transport enhancer" encompasses a plurality of transport enhancers as well as a single transport enhancer. Reference to "a chelating agent" includes reference to two or more chelating agents as well as a single chelating agent, and so forth. In this specification and in the claims that follow, reference will be made to a number of terms, which shall be defined to have the following meanings:

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause. Unless otherwise indicated herein, either explicitly or by implication, if the term "treatment" (or "treating") is used without reference to possible prevention, it is intended that prevention be encompassed as well.

"Optional" or "optionally present"—as in an "optional substituent" or an "optionally present additive" means that the subsequently described component (e.g., substituent or additive) may or may not be present, so that the description includes instances where the component is present and instances where it is not.

By "pharmaceutically acceptable" is meant a material that is not biologically or otherwise undesirable, e.g., the material may be incorporated into a formulation of the invention without causing any undesirable biological effects or interacting in a deleterious manner with any of the other components of the dosage form formulation. However, when the term "pharmaceutically acceptable" is used to refer to a pharmaceutical excipient, it is implied that the excipient has met the required standards of toxicological and manufacturing testing and/or that it is included on the Inactive Ingredient Guide prepared by the U.S. Food and Drug Administration. As explained in further detail infra, "pharmacologically active" (or simply "active") as in a "pharmacologically active" derivative or analog refers to derivative or analog having the same type of pharmacological activity as the parent agent.

As used herein, the term "antigen" is defined as any substance capable of eliciting an immune response.

As used herein, the term "immunogen" refers to an antigen or a substance capable of inducing production of an antigen, such as a DNA vaccine.

As used herein, the term "immunogenicity" refers to the ability of an immunogen, antigen, or vaccine to stimulate an immune response.

As used herein, the term "immunotherapy" refers to an array of treatment strategies based upon the concept of modulating the immune system to achieve a prophylactic and/or therapeutic goal.

As used herein, the term "cytokine" refers to any of numerous small, secreted proteins that regulate the intensity and duration of the immune response by affecting immune cells differentiation process usually involving changes in gene expression by which a precursor cell becomes a distinct specialized cell type. Cytokines have been variously named as lymphokines, interleukins, and chemokines, based on their presumed function, cell of secretion, or target of action. For example, some common interleukins include, but are not limited to, IL-12, IL-18, IL-2, IFN-γ, TNF, IL-4, IL-10, IL-13, IL-21 and TGF-β.

As used herein, the term "chemokine" refers to any of various small chemotactic cytokines released at the site of infection that provide a means for mobilization and activation of lymphocytes. Chemokines attract leukocytes to infection sites. Chemokines have conserved cysteine residues that allow them to be assigned to four groups. The groups, with representative chemokines, are C-C chemokines (RANTES, MCP-1, MIP-1α, and MIP-1β), C-X-C chemokines (IL-8), C chemokines (Lymphotactin), and CXXXC chemokines (Fractalkine).

As used herein, the term "epitope" is defined as the parts of an antigen molecule which contact the antigen binding site of an antibody or a T cell receptor.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the term "immunologic adjuvant" refers to a substance used in conjunction with an immunogen which enhances or modifies the immune response to the immunogen. α-GalCer analogs are used as immunologic adjuvants to modify or augment the effects of a vaccine by stimulating the immune system of a patient who is administered the vaccine to respond to the vaccine more vigorously. In an exemplary implementation, the analog C34 is used as an adjuvant. As used herein, the term "alum adjuvant" refers to an aluminum salt with immune adjuvant activity. This agent adsorbs and precipitates protein antigens in solution; the resulting precipitate improves vaccine immunogenicity by facilitating the slow release of antigen from the vaccine depot formed at the site of inoculation.

As used herein, the term "anti-tumor immunotherapy active agent" refers to antibody generated by a vaccine of the of the present disclosure that inhibits, reduces and/or eliminates tumors.

As used herein, the term "antigen specific" refers to a property of a cell population such that supply of a particular antigen, or a fragment of the antigen, results in specific cell proliferation.

As used herein, the term "Flow cytometry" or "FACS" means a technique for examining the physical and chemical properties of particles or cells suspended in a stream of fluid, through optical and electronic detection devices.

Amino acid residues in peptides shall hereinafter be abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. For further description of amino acids, please refer to Proteins: Structure and Molecular Properties by Creighton, T. E., W.H. Freeman & Co., New York 1983.

The compositions disclosed herein can be included in a pharmaceutical or nutraceutical composition together with additional active agents, carriers, vehicles, excipients, or auxiliary agents identifiable by a person skilled in the art upon reading of the present disclosure.

The compositions disclosed herein can be included in a pharmaceutical or immunogenic composition together with additional active agents, carriers, vehicles, excipients, or auxiliary agents identifiable by a person skilled in the art upon reading of the present disclosure.

The pharmaceutical or immunogenic compositions preferably comprise at least one pharmaceutically acceptable carrier. In such pharmaceutical compositions, the compositions disclosed herein form the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Subject as used herein refers to humans and non-human primates (e.g., guerilla, macaque, marmoset), livestock animals (e.g., sheep, cow, horse, donkey, and pig), companion animals (e.g., dog, cat), laboratory test animals (e.g., mouse, rabbit, rat, guinea pig, hamster), captive wild animals (e.g., fox, deer), and any other organisms who can benefit from the agents of the present disclosure. There is no limitation on the type of animal that could benefit from the presently described agents. A subject regardless of whether it is a human or non-human organism may be referred to as a patient, individual, animal, host, or recipient.

Pharmaceutical compositions suitable for an injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition should be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

By an "effective" amount or a "therapeutically effective" amount of an active agent is meant a nontoxic but sufficient amount of the agent to provide a beneficial effect. The amount of active agent that is "effective" will vary from subject to subject, depending on the age and general condition of the individual, the particular active agent or agents, and the like. Unless otherwise indicated, the term "therapeutically effective" amount as used herein is intended to encompass an amount effective for the prevention of an adverse condition and/or the amelioration of an adverse condition, i.e., in addition to an amount effective for the treatment of an adverse condition.

As defined herein, a therapeutically effective amount of the active compound (i.e., an effective dosage) may range from about 0.001 to 100 g/kg body weight, or other ranges that would be apparent and understood by artisans without undue experimentation. The skilled artisan will appreciate that certain factors can influence the dosage and timing required to effectively treat a subject, including but not limited to the severity of the disease or disorder, previous treatments, the general health or age of the subject, and other diseases present.

An adverse condition as that term is used herein may be a "normal" condition that is frequently seen in individuals or a pathologic condition that may or may not be associated with a named disease.

As used herein, the term "lipid" refers to any fat-soluble (lipophilic) molecule that participates in cell signaling pathways.

As used herein, the term "glycolipid" refers to a carbohydrate-attached lipid that serves as a marker for cellular recognition.

According to another aspect, one or more kits of parts can be envisioned by the person skilled in the art, the kits of parts to perform at least one of the methods herein disclosed, the kit of parts comprising two or more compositions, the compositions comprising alone or in combination an effective amount of the compositions disclosed herein according to the at least one of the above mentioned methods.

The kits possibly include also compositions comprising active agents, identifiers of a biological event, or other compounds identifiable by a person skilled upon reading of the present disclosure. The kit can also comprise at least one composition comprising an effective amount of the compositions disclosed herein or a cell line. The compositions and the cell line of the kits of parts to be used to perform the at least one method herein disclosed according to procedure identifiable by a person skilled in the art.

As used herein, the term "polypeptide" refers to any multimer or polymer of amino acid residues. A polypeptide may be composed of two or more polypeptide chains. A polypeptide includes a protein, a peptide, and an oligopeptide. A polypeptide can be linear or branched. A polypeptide can comprise modified amino acid residues, amino acid analogs or non-naturally occurring amino acid residues and can be interrupted by non-amino acid residues. Included within the definition are amino acid polymers that have been modified, whether naturally or by intervention, e.g., formation of a disulfide bond, glycosylation, lipidation, methylation, acetylation, phosphorylation, or by manipulation, such as conjugation with a labeling component.

As used herein, the term "specifically binding," refers to the interaction between binding pairs (e.g., an antibody and an antigen). In various instances, specifically binding can be embodied by an affinity constant of about $10^{-6}$ moles/liter, about $10^{-7}$ moles/liter, or about $10^{-8}$ moles/liter, or less.

As will be apparent to those of skill in the art upon reading this invention, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

Unless otherwise defined, all technical and scientific terms used herein have the same meaning as commonly understood by one of ordinary skill in the art to which this invention pertains. In the case of conflict, the present document, including definitions will control.

Fucose-Enriched Polysaccharide Fraction (FMS) Isolated from Reishi

Recent findings revealed that specific B cell subsets could establish memory for providing specific immunoglobulin (Ig) synthesis in response to TI-associated polysaccharides (12-14). In an attempt to understand the biological significance of polysaccharides derived from natural sources, a crude extract fraction of water-soluble and fucose-containing polysaccharides (F3) from *Ganoderma lucidum* (Reishi, a mushroom that has been long utilized as a herb medicine) were previously isolated and characterized (15). F3 has since been shown essential for regulation of cytokine network, IgM production and hematopoietic cell expansion (16-19).

Several pattern recognition receptors that could interact with F3, including Dectin-1, DC-SIGN, Langerin, Kupffer cell receptor, macrophage mannose receptor and Toll-like receptors have been identified (20). Notably, these results supported the idea that F3 activates the immune response likely by interacting with carbohydrate-recognizing receptors. In animal studies, F3 is reported to serve as a vaccine adjuvant and exert anti-tumor activities through an enhancement of the host-mediated immunity (21), leading to an interesting question of whether and how antibody-mediated immunity plays a role in the anti-tumor activity of F3 in mice.

In the current study, fucose-enriched F3 polysaccharides (FMS) were used as immunogens and the results showed that the induced antisera could recognize biologically relevant glycans, in particular tumor-associated glycan epitopes, supporting the hypothesis that terminal fucosylation on Reishi polysaccharides plays a critical role in the anti-tumor responses.

Anti-Tumor Activity of Reishi F3

We first conducted a study in an animal tumor model using C57BL/6J mice with implantation of murine Lewis lung carcinoma (LLC1) cells to investigate the anti-tumor activity of F3. Briefly, LLC1 cells were subcutaneously (s.c.) transplanted into mice, and then F3 (24, 52, 120 and 240 mg/kg of body weight per mouse dissolved in PBS) was administered intraperitoneally (i.p.) once every other day; and the process was repeated for 28 days.

Figure 5:
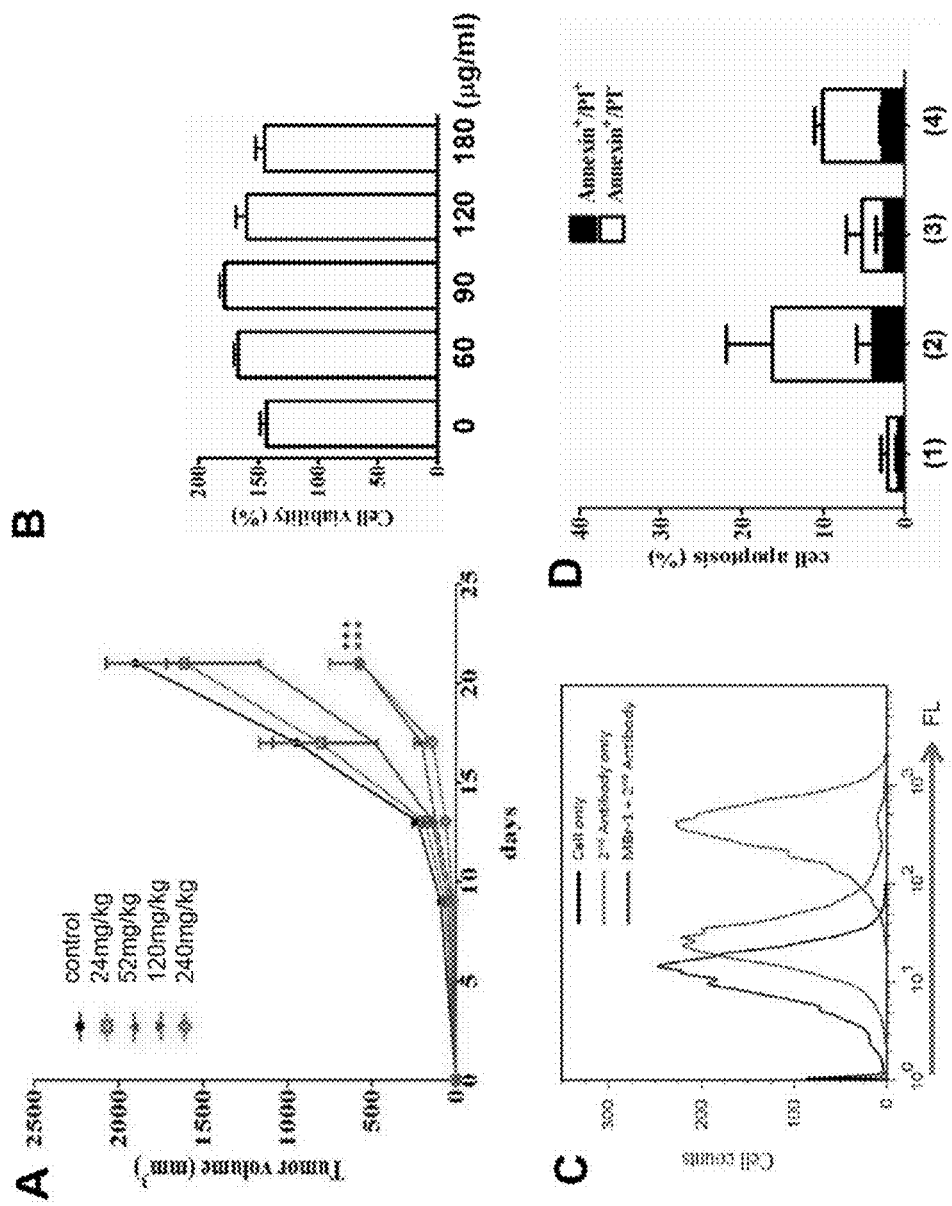
FIG. 5. Anti-tumor effects of F3. (A) C57BL/6 mice were injected s.c. with LLC1 cells ($2 \times 10^5$), then were treated i.p. with F3 (24, 52, 120 and 240 mg/kg of body weight per mouse) for 21 days at intervals of 2 days. Tumor volume curves were expressed as mean±s.e.m. (n=4~6 for each group). Statistical analysis of tumor growth compared with control (PBS-treated mice) was shown. ***p<0.001. (B) LLC1 cells ($1 \times 10^3$) in vitro were treated with F3 (0, 60, 90, 120, and 180 μg/ml) for 24 h, the viability of cells was determined by 3-(4,5-dimethylthiazol-2-yl)-2,5-diphenyltetrazolium bromide (MTT) assay. The viability of un-treated cells was normalized as 100%. Data were expressed as mean±s.e.m. (n=4). (C) Identification of Globo H expressed on LLC1 cells was detected by mAb MBr1 and analyzed by flow cytometry. In the histogram, cell numbers are presented on the y axis, and fluorescence intensity (a logarithmic scale) is plotted on the x axis. The positive cells were stained with DyLight-649 conjugated MBr1 (red line). Nonspecific binding control was performed with only secondary mAb (blue line). The cells in PBS (containing 5% BSA) represented blank (black line). (D) The F3-induced antisera trigger complement-mediated LLC1 cell lysis in vitro. The cells were cultured in the presence of 10% antisera from four groups: (1) PBS-treated mice; (2) F3-treated mice; (3) LLC1-bearing mice, and (4) F3-treated/LLC1-bearing mice. After 1 h at 37° C. incubation, the cells were stained with FITC-conjugated annexin V and counterstained with PI (propidium iodide) in order to detect early apoptotic and late apoptotic cells by flow cytometry. The early apoptotic cells (%) were shown annexin V-FITC$^+$ and PI$^-$, and the late apoptotic cells (%) were double positive for annexin V-FITC and PI.

As shown in the tumor growth curves (FIG. 5A), F3 exhibited a significant inhibition against the growth of LLC1 cells in a dose-dependent manner, and the most effective inhibitory response was observed in the dosage between 120 and 240 mg/kg, which is a feasible daily dose in humans. However, MTT assay results revealed that F3 (<200 µg/ml) had no significant effect on LLC1 cell viability as compared to the un-treated cells (FIG. 5B). These results suggested that F3 may suppress the LLC1 cell growth and prolong the survival rate of tumor-bearing mice via an indirect anti-tumor mechanism. In animal studies, the anti-tumor effects of polysaccharides extracted from Reishi were reported previously (22, 23).

Figure 6:
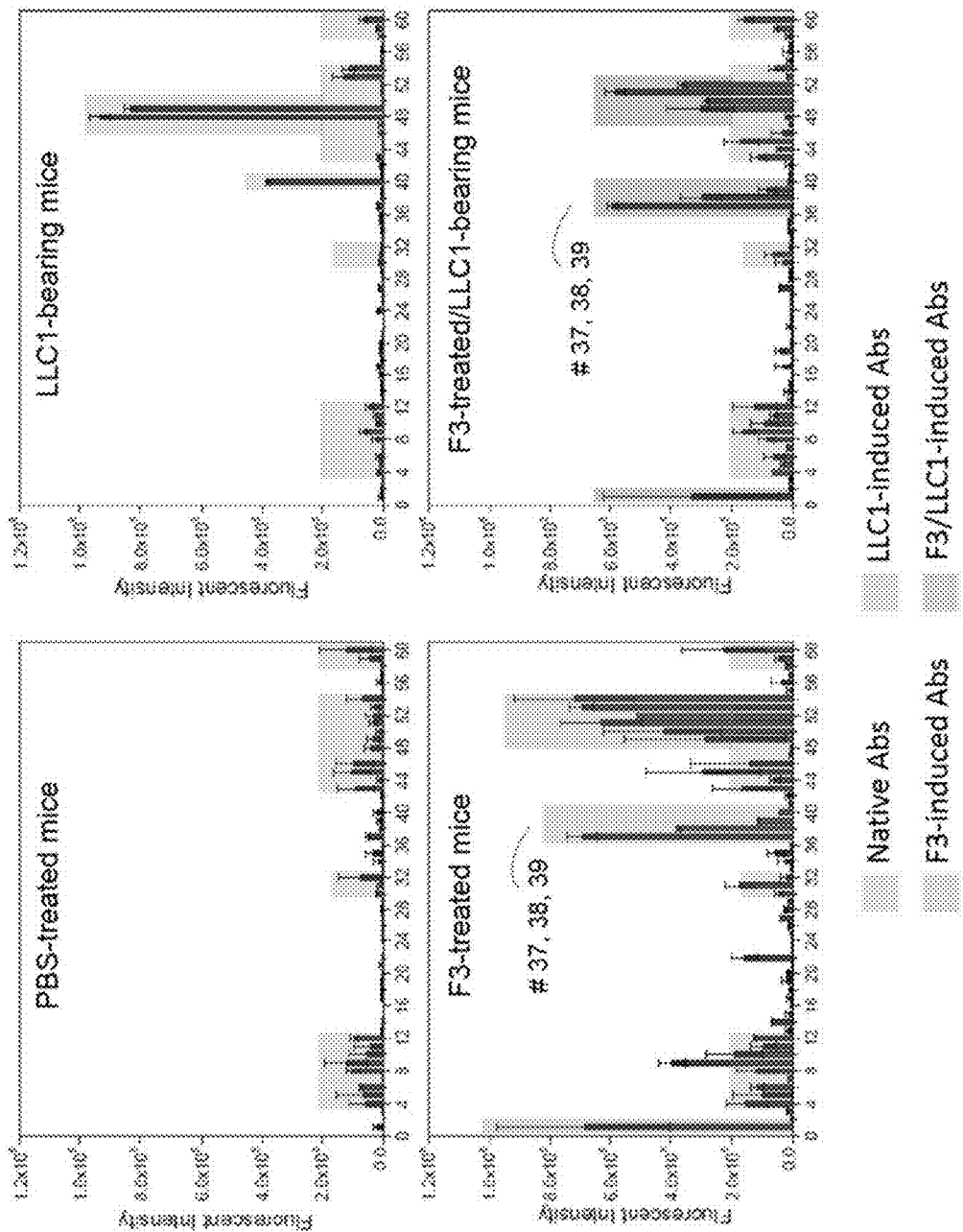
FIG. 6. Glycan microarray analysis of F3-treated mice sera (i.p. 120 mg/kg of body weight). The test antisera (on Day $14^{th}$ after first injection) were obtained from four experimental conditions: PBS-treated mice, F3-treated mice, LLC1-bearing mice, and F3-treated/LLC1-bearing mice. The glycan binding patterns of serum IgM antibodies to an array of 60 synthetic oligosaccharides was measured. Data represent mean±SD (n=4-6 for each group). Notable differences with respect to the IgM-bound Globo H-series glycans marked with glycan numbers are indicated. A list describing the 60 structurally different oligosaccharides present in the array is provided in FIG. 7.
Figure 7:
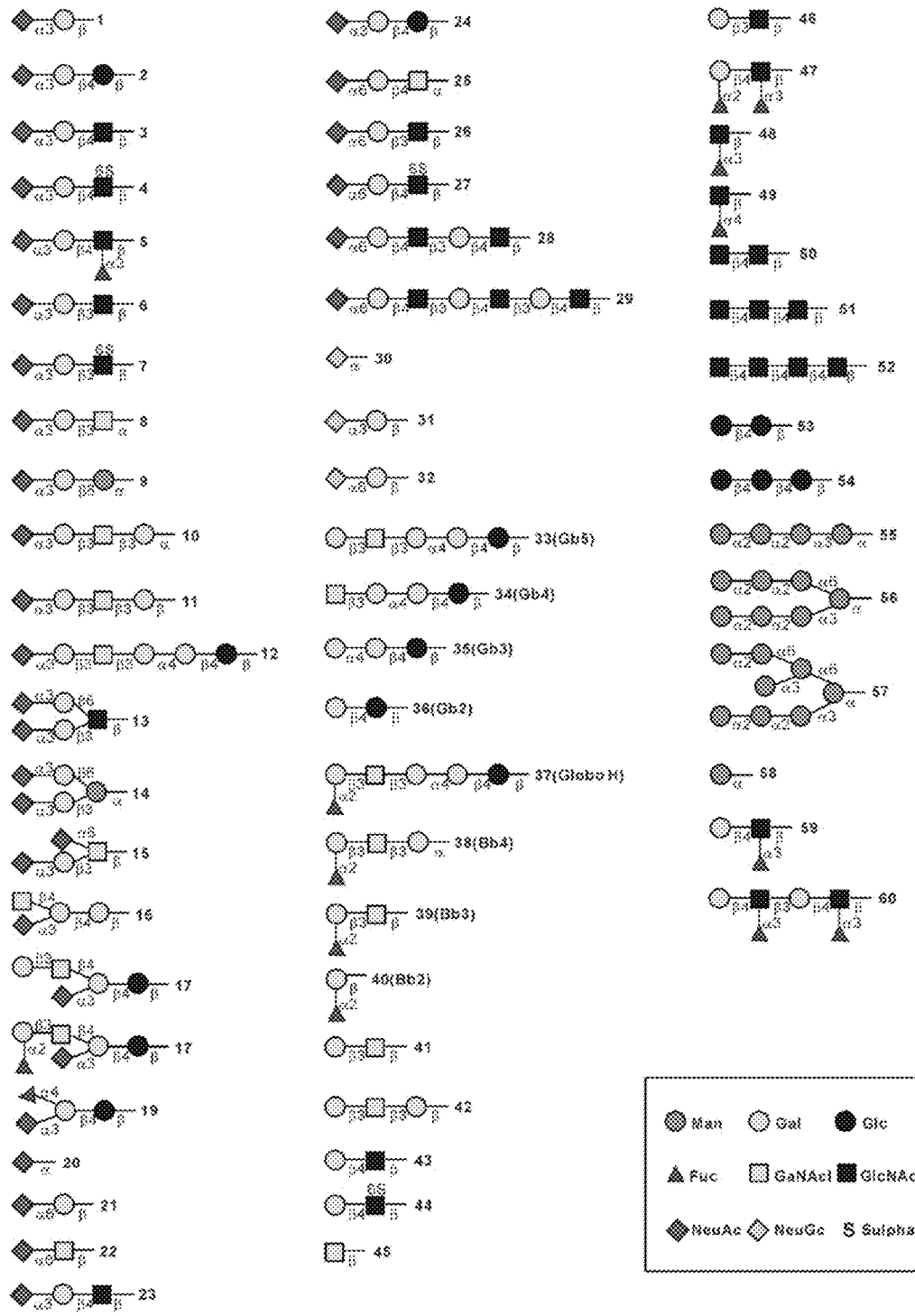
FIG. 7. A list of 60 glycan structures marked with glycan number to the NHS-functionalized glass surface of the fabricated glycan chips.

More interestingly, there was evidence that the sera from Reishi polysaccharide-treated mice markedly inhibited murine sarcoma-180 and human lung carcinoma (PG) growth in vitro, but the pure Reishi extract alone did not induce similar effects (24, 25). Thus, we conducted a synthetic glycan microarray analysis to investigate if F3-induced antisera could recognize biologically important glycan epitopes. The serum samples were screened at a weekly interval with 60 structurally different synthetic oligosaccharides, including several tumor-associated glycans. Given the glycan binding patterns of F3-induced antisera, there was a clear trend showing the increase in the binding affinity of IgM antibodies to Globo H and Globo H-series glycans, including the terminal tetrasaccharide (Bb4) and trisaccharide (Bb3), after two weeks of F3 treatment as compared to the control (without F3 treatment) (FIG. 6 and saccharide structures are shown in FIG. 7).

Contrary to IgM responses, the serum IgG had no appreciable glycan-binding effects. So far, the IgM anti-Globo H monoclonal antibody (mAb), MBr1, is one of the valuable probes for Globo H-containing glycoconjugate detection (26, 27) and it also has been known to exert complement-dependent cytotoxicity (CDC) against Globo H-positive tumors (8, 28). Thus, we examined the expression levels of Globo H antigens on the LLC1 cell surface by mAb MBr1 immunostaining (FIG. 5C). The addition of F3-induced antisera to LLC1 cells was found to trigger cell death in vitro (FIG. 5D), leading to a speculation that F3 has the potential to induce antibody-mediated anti-tumor activity.

Fucose-Enriched Polysaccharide Fraction (FMS) Isolated from Resihi Induces Antibodies Recognizing Globo H-Series Structures.

One embodiment of this invention is a method of treating cancer by administering to a subject in need thereof an effective amount of an immune composition containing FMS and an adjuvant. The types of target cancer include, but are not limited to, breast cancer (including stages 1-4), lung cancer (e.g., small cell lung cancer), liver cancer (e.g., hepatocellular carcinoma), oral cancer, stomach cancer (including T1-T4), colon cancer, nasopharynx cancer, skin cancer, kidney cancer, brain tumor (e.g., astrocytoma, glioblastoma multiforme, and meningioma), prostate cancer, ovarian cancer, cervical cancer, bladder cancer, and endometrium, rhabdomyosarcoma, osteosarcoma, leiomyosarcoma, and gastrointestinal stromal tumor.

Optionally, an adjuvant was included with the FMS in the immunogenic compositions. In some embodiments, the adjuvant was a glycolipid. Preferred adjuvants include, but are not limited to synthetic analogs of α-GalCer, such as: 7DW8-5 and C34.

Previous reports indicated that the fucosylation on polysaccharides is responsible for the immune-modulating activity of F3 (15). Because F3 is known to be a heterogeneous and high-molecular-weight polysaccharide (>100 kDa), we therefore purified a fucose-enriched polysaccharide fraction from F3, namely FMS, by a series of chromatographic steps.

Using SEC/MALLS (size-exclusion chromatography combined with multi-angle laser light scattering) system, the average molecular mass of FMS was estimated to be 35 kDa.

The composition analysis showed that FMS predominantly consists of fucose, xylose, galactose and mannose in the ratio of 2:1.5:2.5:3.5, along with a small amount of glucose and amino-sugars (such as glucosamine and galactosamine). Methylation analysis indicated FMS is based on a 1,4-mannan backbone with side chains at the C3-position, and a 1,6-α-galactan branched at the C2-position and is highly decorated with terminal fucose (Table 3) (29-31).

Figure 1:
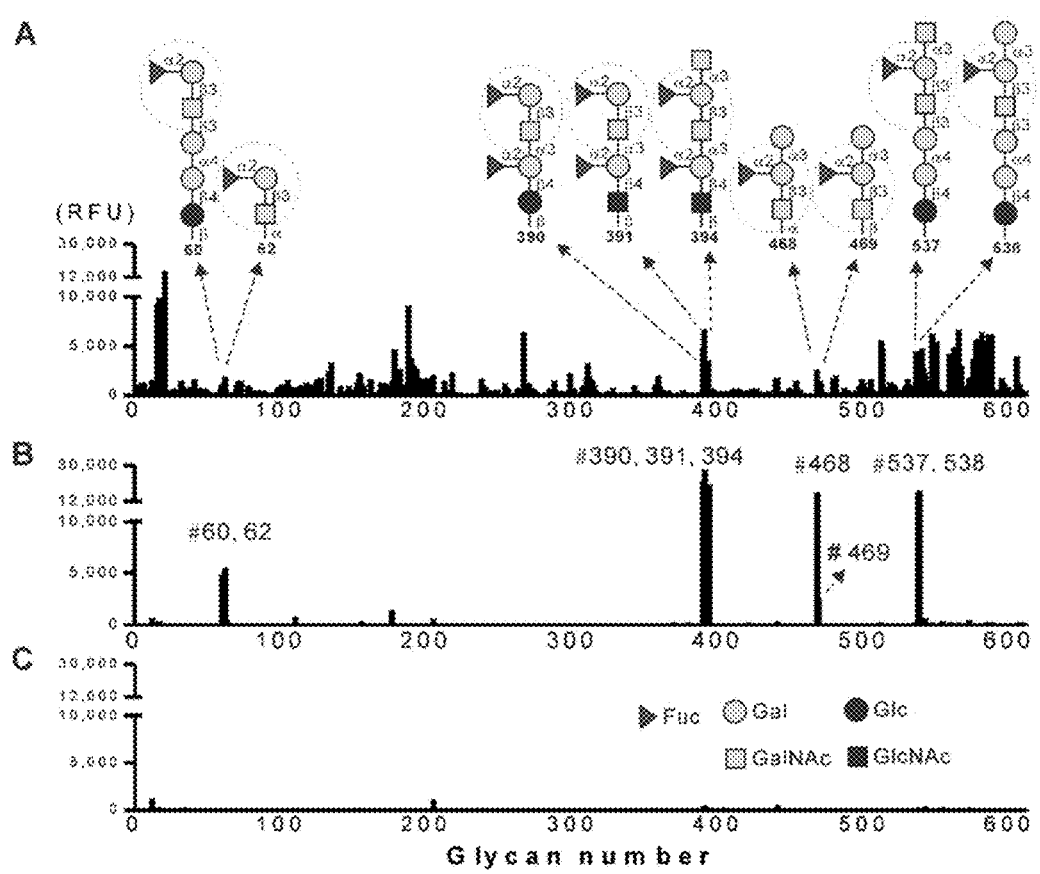
FIG. 1 shows glycan-binding patterns of the serum IgM antibodies as measured by the CFG glycan microarray. Each histogram represents different sources of IgM binding to the glycan microarray, where the x-axis shows the glycan number of 611 saccharides examined and the y-axis is relative fluorescent units (RFU). Serum samples (tested at 1:100 dilution) from (A) F3-, (B) FMS- and (C) PBS-treated mice were collected on Day $14^{th}$ after four dose injections and analyzed by printed array Version 5.0 of the Consortium for Functional Glycomics Core H. Nine of the identified glycan structures marked with glycan numbers are indicated. Dashed circles indicate the consensus glycan epitope (H-type 3/4 structure). Bars show the average RFUs. n=4 (A, B); n=2 (C).

To examine the glycan-binding properties of FMS-induced antisera, a more comprehensive glycan microarray with 611 glycans from the Consortium for Functional Glycomics (CFG) Core H was used to assess the contribution of serum IgM antibodies. We examined 2nd week serum samples obtained from FMS- and F3-treated mice, respectively. The sera of control mice (PBS-treated) were also concurrently analyzed to determine the background of non-specific binding. The 611 glycan-binding profiles as indicated by relative fluorescence units (RFUs) are depicted in FIG. 1. It is evident that the anti-glycan IgM antibodies of FMS group have higher specificity and selectivity than those of the F3 group for several glycans, including glycan numbers (#) 60, 62, 390, 391, 394, 468, 469, 537 and 538. A detailed list of the top 30 glycans bound by the F3 group is also deposited in Table 2.

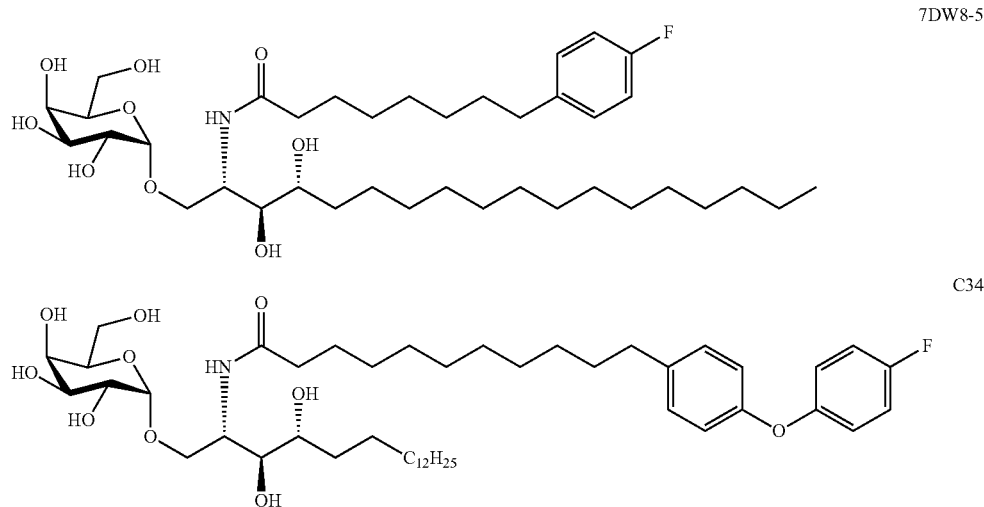

TABLE 2

List of top 30 glycans bound by F3-induced sera IgM as ranked in decreasing order of binding intensities.

| CFG glycan (no.)[a] | Relative fluorescence units mean ± s.e.m. (n = 4) |
|---|---|
| GlcNAcβ1-6(GlcNAcβ1-4)(GlcNAcβ1-3)GlcNAc-Sp8 (21) | 14,793 ± 2,522 |
| Neu5Acα2-6GalNAcβ1-4GlcNAcβ-Sp0 (267) | 12,617 ± 3,963 |
| GlcNAcβ-Sp8 (17) | 9,817 ± 1,608 |
| GlcNAcβ-Sp0 (16) | 9,187 ± 1,774 |
| GlcNAcβ1-6(GlcNAcβ1-4)GalNAcα-Sp8 (188) | 9,038 ± 1,680 |
| Fucα1-2Galβ1-3GalNAcα1-3(Fucα1-2)Galβ1-4GlcNAcβ-Sp0 (391) | 6,581 ± 250.0 |
| GlcNAcβ1-4GlcNAcβ-Sp12 (312) | 6,566 ± 2,791 |
| GlcNAcβ1-3Galβ1-4GlcNAcβ1-3Galβ1-4GlcNAcβ-3Galβ1-4GlcNAcβ1-3Galβ1-4GlcNAcβ1-2Manα-6(GlcNAcα1-3Galβ1-4GlcNAcβ1-3Galβ1-4GlcNAcβ1-3Galβ1-4GlcNAcβ1-3Galβ1-4GlcNAcβ1-2Manα1-3)Manβ1-4GlcNAcβ1-4GlcNAcβ-Sp26 (566) | 6,531 ± 941.0 |
| GlcNAcβ1-3Galβ1-4GlcNAcβ1-3Galβ1-4GlcNAcβ1-3Galβ1-4GlcNAcβ1-3Galβ1-4GlcNAcβ1-2Manα1-6(GlcNAcβ1-3Galβ1-4GlcNAcβ1-3Galβ1-4GlcNAcβ1-3Galβ1-4GlcNAcβ1-3Galβ1-4GlcNAcβ1-2Manα1-3)Manβ1-4GlcNAcβ1-4(Fucα1-6)GlcNAcβ-Sp19 (581) | 6,292 ± 991.0 |
| GlcNAcβ1-3Galβ1-4GlcNAcβ1-3Galβ1-4GlcNAcβ1-2Manα1-6(GlcNAcβ1-3Galβ1-4GlcNAcβ1-3Galβ1-4GlcNAcβ1-2Manα1-3)Manβ1-4GlcNAcβ1-4GlcNAcβ-Sp25 (547) | 6,164 ± 502.0 |
| GlcNAcβ1-3Galβ1-4GlcNAcβ1-3Galβ1-4GlcNAcβ1-3Galβ1-4GlcNAcβ1-3Galβ1-4GlcNAcβ1-6(GlcNAcβ1-3Galβ1-4GlcNAcβ1-3Galβ1-4GlcNAcβ1-3Galβ1-4GlcNAcβ1-3Galβ1-4GlcNAβ1-2)Manα1-6(GlcNAcβ1-3Galβ1-4GlcNAcβ1-3Galβ1-4GlcNAcβ1-3Galβ1-4GlcNAcβ1-3Galβ1-4GlcNAcβ1-2Manα1-3)Manβ1-4GlcNAcβ1-4(Fucα1-6)GlcNAcβ-Sp24 (588) | 6,088 ±± 1,119 |
| GlcNAcβ1-3Galβ1-4GlcNAcβ1-3Galβ1-4GlcNAcβ1-3Galβ1-4GlcNAcβ1-6(GlcNAcβ1-3Galβ1-4GlcNAcβ1-3Galβ1-4GlcNAcβ1-3Galβ1-4GlcNAβ1-2)Manα1-6(GlcNAcβ1-3Galβ1-4GlcNAcβ1-3Galβ1-4GlcNAcβ1-3Galβ1-4GlcNAcβ1-2Manα1-3)Manβ1-4GlcNAcβ1-4(Fucα1-6)GlcNAcβ-Sp24 (586) | 6,048 ± 1,081 |
| GlcNAcβ1-3Galβ1-4GlcNAcβ1-3Galβ1-4GlcNAcβ1-3Galβ1-4GlcNAcβ1-2Manα1-6(GlcNAcβ1-3Galβ1-4GlcNAcβ1-3Galβ1-4GlcNAcβ1-3Galβ1-4GlcNAcβ1-2Manα1-3)Manβ1-4GlcNAcβ1-4(Fucα1-6)GlcNAcβ-Sp24 (579) | 5,598 ± 951.0 |
| GlcNAcβ1-3Galβ1-4GlcNAcβ1-3Galβ1-4GlcNAcβ1-2Manα1-6(GlcNAcβ1-3Galβ1-4GlcNAcβ1-3Galβ1-4GlcNAcβ1-2Manα1-3)Manβ1-4GlcNAcβ1-4(Fucα1-6)GlcNAcβ-Sp24 (577) | 5,535 ± 782.0 |
| GlcNAcβ1-3Galβ1-4GlcNAcβ1-3Galβ1-4GlcNAcβ1-6(GlcNAcβ1-3Galβ1-4GlcNAcβ1-3Galβ1-4GlcNAβ1-2)Manα1-6(GlcNAcβ1-3Galβ1-4GlcNAcβ1-3Galβ1-4GlcNAcβ1-2Manα1-3)Manβ1-4GlcNAcβ1-4(Fucα1-6)GlcNAcβ-Sp24 (584) | 5,468 ± 989.0 |
| (6S)(4S)GalNAcβ1-4GlcNAc-Sp8 (512) | 5,446 ± 1,586 |
| GlcNAcβ1-3Galβ1-4GlcNAcβ1-3Galβ1-4GlcNAcβ1-3Galβ1-4GlcNAcβ1-2Manα1-6(GlcNAcβ1-3Galβ1-4GlcNAcβ1-3Galβ1-4GlcNAcβ1-3Galβ1-4GlcNAcβ1-2Manα1-3)Manβ1-4GlcNAcβ1-4GlcNAcβ-Sp25 (550) | 5,329 ± 1,162 |
| GlcNAcβ1-3Galβ1-4GlcNAcβ1-6(GlcNAcβ1-3Galβ1-3)GalNAcα-Sp14 (582) | 4,782 ± 1,755 |
| Fucα1-2Galβ1-3GalNAcα1-3(Fucα1-2)Galβ1-4Glcβ-Sp0 (390) | 4,690 ± 230.0 |
| (6S)GalNAcβ1-4GlcNAc-Sp8 (513) | 4,650 ± 1,555 |
| GlcNAcβ1-3Galβ1-4GlcNAcβ1-2Manα1-6(GlcNAcβ1-3Galβ1-4GlcNAcβ1-2Manα1-3)Manβ1-4GlcNAcβ-Sp12 (540) | 4,622 ± 337.0 |
| GlcNAcβ1-5(GlcNAcβ1-3)GalNAcα-Sp14 (178) | 4,536 ± 759.0 |
| GlcNAcβ1-3Galβ1-4GlcNAcβ1-6(GlcNAcβ1-3)Galβ1-4GlcNAc-Sp0 (536) | 4,341 ± 1,000 |
| GlcNAcβ1-3Galβ1-4GlcNAcβ1-6(GlcNAcβ1-3Galβ1-4GlcNAcβ1-2)Manα1-6(GlcNAcβ1-3Galβ1-4GlcNAcβ1-2Manα1-3)Manβ1-4GlcNAcβ1-4GlcNAc-Sp24 (559) | 4,102 ± 729.0 |
| GlcNAcβ1-6(Neu5Acα2-3Galβ1-3)GalNAcα-Sp14 (605) | 3,866 ± 1,150 |
| GlcNAcβ1-4GlcNAcβ1-4GlcNAcβ1-4GlcNAcβ1-4GlcNAcβ1-4GlcNAcβ1-Sp8 (190) | 3,692 ± 1,572 |
| GlcNAcβ1-3Galβ1-4GlcNAcβ1-2Manα1-6(GlcNAcβ1-3Galβ1-4GlcNAcβ1-2Manα1-3)Manβ1-4GlcNAcβ1-4(Fucα1-6)GlcNAcβ-Sp24 (575) | 3,573 ± 109.0 |
| GalNAcα1-3(Fucα1-2)Galβ1-3GalNAcα1-3(Fucα1-2)Galβ1-4GlcNAcβ-Sp0 (394) | 3.421 ± 245.0 |
| GlcNAcβ1-6(Galβ1-3)GalNAcα-Sp14 (135) | 3,202 ± 224.0 |
| GlcNAcβ1-4GlcNAcβ-Sp10 (311) | 3,140 ± 1,393 |

[a]Each glycan structure with chemical linker is printed on the CFG array Version 5.0. Structure of the linker Is indicated, sp0 = (CH2)2NH2; sp9 = (CH2)5NH2; sp21 = N(CH3)OCH2CH2NH2.

Although the exact antigen that affects the antibody binding avidity is not clear, it becomes apparent that these top ranked glycans bound by FMS-induced antisera all shared a common structure in the non-reducing termini, i.e., Fucα1-2Galβ1-3GalNAc-R. More interestingly, a group of glycans (##390, 391 and 394) was found to display the highest antibody binding intensities, suggesting that an additional disaccharide (Fucα1-2Gal) extension in the reducing end of Fucα1-2Galβ1-3GalNAc-R improves the antisera binding affinity.

Figure 2:
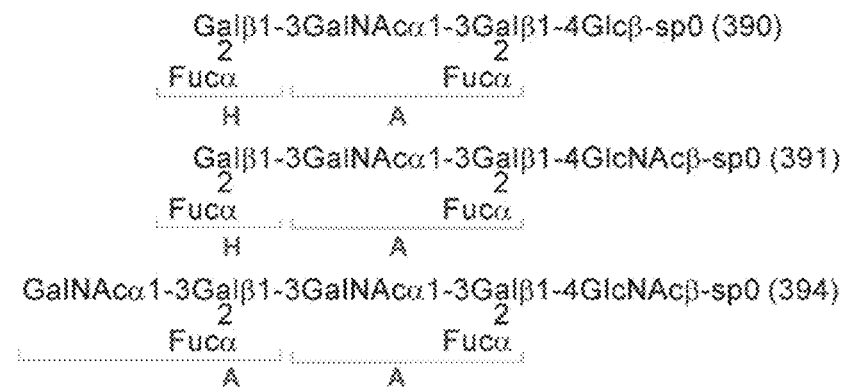
FIG. 2. A spectrum of tumor associated-glycans highly recognized by FMS-induced antisera. Each glycan structure with chemical linker is printed on the CFG Version 5.0, which was classified into two groups. Structures of the linkers are indicated; sp0=$CH_2CH_2NH_2$; sp9=$CH_2CH_2CH_2CH_2CH_2NH_2$; sp21=$N(CH_3)OCH_2CH_2NH_2$. Definition of blood group determinants (H, A or B) is annotated.
Figure 2:

Next, we asked if any highly recognized glycans are related to endogenous human tumor-associated antigens. The identity of these glycan structures and their biological source, when further categorized, indicates that most of them represent blood group ABH determinants exclusively found in human glycosphingolipids (GSLs) (FIG. 2) (32-34). The three glycans, #390, 391 and 394, have characteristic determinants that belong to terminal glycan structures of GSL neolacto-series (type 3 chain). It has been reported that differences in the distribution of such GSL glycans between normal and cancerous tissues can be used for the diagnosis of human cervical carcinoma and bladder tumors (35, 36).

In addition, the other three glycans that were identified as tumor-associated antigens belong to the members of GSL globo-series structures (type 4 chain), including Globo H (#60), Globo A (#537) and Globo B (#538). This may be the manifestation of well-known cross-reactivity of carbohydrate-specific antibodies which lead us to speculate that the glycan moiety, Fucα1-2Galβ1-3GalNAcα/β (termed by H-type 3/4) is likely the antigenic determinant underlying the observed specificity of the FMS-induced IgM antibodies, i.e. the antibodies recognize Globo H and the related tumor-associated glycans (extended Globo H-series).

Terminal Fucose of FMS is Important for Antibody-Mediated Anti-Tumor Efficacy

Figure 3:
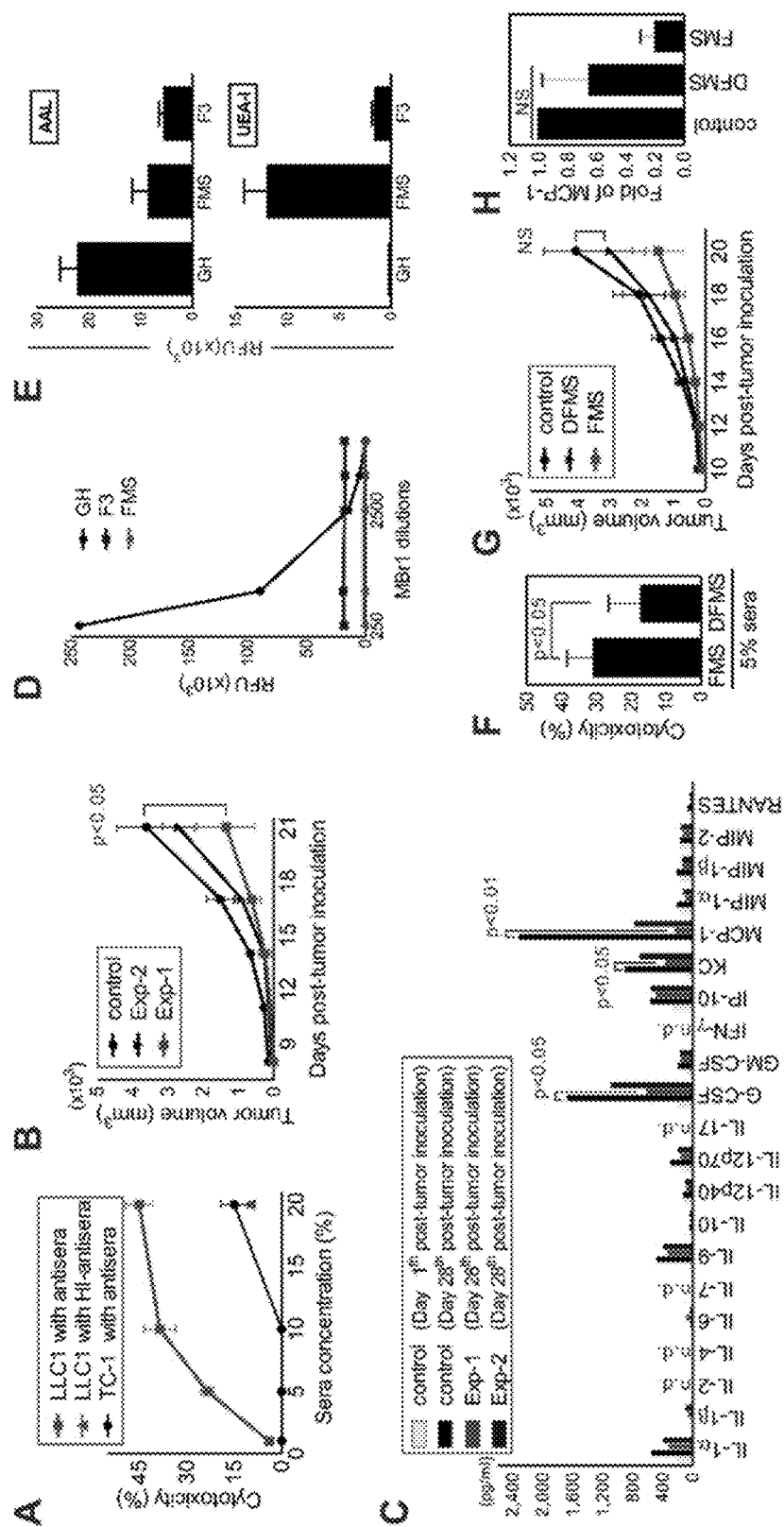
FIG. 3. Anti-tumor activities of fucose-enriched F3 polysaccharides, FMS. (A) Antibody-mediated cytotoxicity (CDC) of antisera from FMS-treated mice to LLC1 and TC-1 tumor cells was determined by LDH kit. The value of antisera heated at 56° C. for 30 min (HI-antisera) is indicative of the complement depletion effect. (B) Comparison of anti-tumor effects between preventive (Exp-1) and therapeutic (Exp-2) FMS treatment in vivo. Control is PBS-treated mice with tumor inoculation. (C) FMS treatment suppressed tumor-associated cytokines and chemokines production in vivo. Serum samples were collected at indicated time after tumor inoculation and examined by Beadlyte mouse 21-pex kits. (D and E) Distinct binding intensities of plant lectins (AAL, 2 μg/ml and UEA-I, 10 μg/ml) and anti-Globo H mAb (MBr1, 0.5 mg/ml) to Globo H (GH), FMS and F3 were determined by using the fabricated glycan microarray. (F, G and H) DFMS (low-fucose content of FMS) treatment reduced CDC (F) and anti-tumor activities in vivo, as assessed by tumor growth curves (G) and MCP-1 production levels (H). Values show the mean±SD (n=3~5 for each experiment). n.d.=not detectable. NS=no statistical significant.
Figure 9:
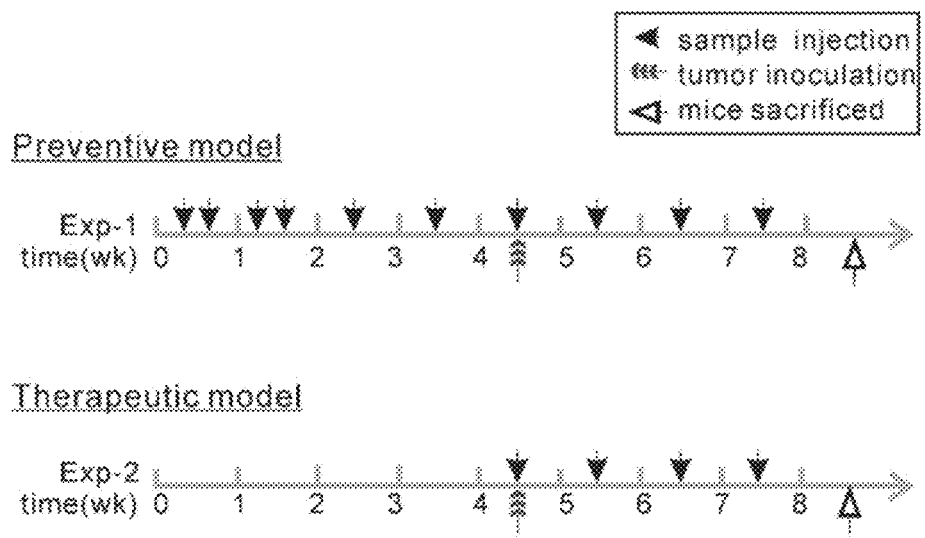
FIG. 9. (9A) Two immunization plans were designed to assess the preventive and therapeutic treatments. (9B) Competition assay for assessing glycan specificities of the FMS-induced sera IgM. Competitor sugars and antisera (test at 1:100 dilution) were added simultaneously to sub-well on the Globo H-printed chips. The percentage of binding was normalized against the antisera without competitors. One representative data from two independent experiments is shown. n=3 replicates FIG. 10. (10A) MALDI-MS mapping and compositional assignments of singly charged sodiated molecular ions of permethylated FMS hydrolysate alditols. (10B) Targeted nanoLC-MS/MS glycan sequencing and fucosylated epitope linkage determination of permethylated alditols of FMS hydrolysate. Base peak chromatograph of FMS-H glycans and extracted ion chromatographs (in color background) for glycan compositions of 1Fuc-2Hex-itol, 1Fuc-1Xy-1Hex-itol and 3Fuc-itol, respectively. NL (normalized level) represents the axial intensity of chromatographs. Analysis of observed m/z and glycan compositions is shown in Table 1.
Figure 9:
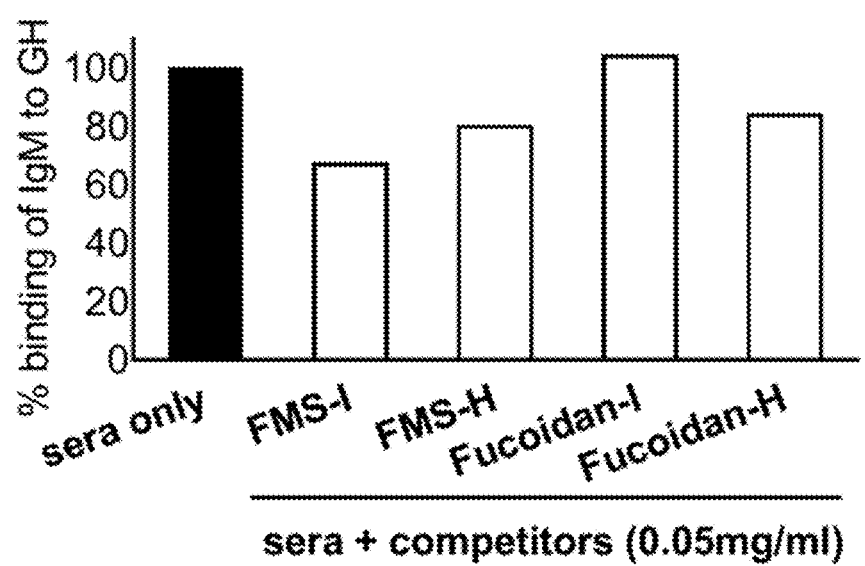

We further studied if the FMS-mediated antibody responses to LLC1 cells could trigger cytotoxicity in vitro, and if such CDC activity is effective to Globo H-positive tumors. A Globo H-negative mouse tumor cell line, TC-1, was also selected for comparison. As shown in FIG. 3A, the results of the CDC assay indicated that LLC1 cells are more sensitive than TC-1 cells to FMS-induced antisera in a concentration-dependent manner. We further investigated if FMS could inhibit the growth of LLC1 cells in vivo. Two immunization plans were designed to assess both the preventive (Exp-1) and therapeutic (Exp-2) potentials as compared with the control, PBS-treated LLC1-bearing mice (FIG. 9A). The resulting tumor growth curves suggested that pretreatment of FMS (Exp-1) could lead to a greater reduction in tumor volume ($p<0.05$ versus control) (FIG. 3B). Since a close association between chronic inflammation and tumor development is often implied, we examined whether FMS dosage may regulate the production of LLC1-associated inflammatory mediators in vivo. After tumor inoculation, a multiplex cytokine profiling showed that two chemokines and one cytokine, monocyte chemoattractant protein-1 (MCP-1), CXCL1 (KC) and granulocyte colony-stimulating factor (G-CSF), respectively, were remarkably decreased in the mice pretreated with FMS (Exp-1) on Day 28th ($p<0.05$ versus Day 28th control) (FIG. 3C), More interestingly, administration of FMS effectively lowered the serum levels of MCP-1 in LLC1-bearing mice. It is known that MCP-1 secreted from tumor cells is an important determinant in the pathogenesis of human lung cancers. Previous studies have also demonstrated that blockade of MCP-1, as mediated by neutralizing antibodies, in several animal models of non-small-cell lung cancer (NSCLC) significantly slowed the growth of primary tumors (37, 38). These results thus supported the notion that FMS could not only suppress the LLC1 cell growth, but also attenuate relative inflammation levels in vivo.

The unexpected abilities of F3 and FMS serving as immunogens to induce antibodies and suppress Globo H-positive tumor growth, together with the glycan microarray analysis, suggest that the unit structure of antigen present in F3 and FMS may be fucosylated glycans. Previous studies demonstrated that the minimal epitope of mAb MBr1 is the H-type 3/4, such as the terminal trisaccharide of Globo H (Fucα1-2Galβ1-3GalNAcβ, also called Bb3), and that the terminal fucose is essential for the antibody recognition (27, 34, 39). To examine if Globo H-series molecules exist in our Reishi polysaccharides, we fabricated saccharide-printed slides by attachment of Globo H (100 μM), F3 (1 mg) and FMS (1 mg) onto NHS-activated glass slides, and then the chips were interrogated with MBr1. As expected, the binding curve of the antibody to Globo H was in a dose-dependent manner. FMS and F3, nonetheless, displayed neither significant binding interaction, nor dose-dependent behavior (FIG. 3D). Regarding to the antibody specificity, we previously reported that Globo H-based glycoconjugate vaccines induced antibodies more selectively for Globo H, SSEA3 (also called Gb5, Galβ1-3GalNAcβ1-3Galα1-4Galβ1-4Glcβ) and SSEA4 (Neu5Acα2-3Galβ1-3GalNAcβ1-3Galα1-4Galβ1-4Glcβ) (9). However, such cross-reactivity was not found in either F3- or FMS-induced IgM antibodies. This led us to think that Reishi polysaccharides may not contain Globo H-series antigens. This was probed with saccharide-printed slides interrogated with two α-L-fucose-specific lectins, UEA-I (*Ulex europaeus* agglutinin-I) and AAL (*Aleuria aurantia* lectin). AAL bound to all the samples, confirming the presence of □-fucosyl linkages. Both FMS and F3 showed significant binding intensities with lectin UEA-I (FIG. 3E), suggesting that the existence of Fucα1-2Gal disaccharide unit. The observed low binding of Globo H is consistent with the previous data showing that the lectin UEA-1 is unreactive to the H-type 3/4 structures (40, 41). Taken together, the results provide evidence that our Reishi polysaccharides contain α-L-fucosylated glycans but may differ from the Globo H-series structures.

Figure 4:
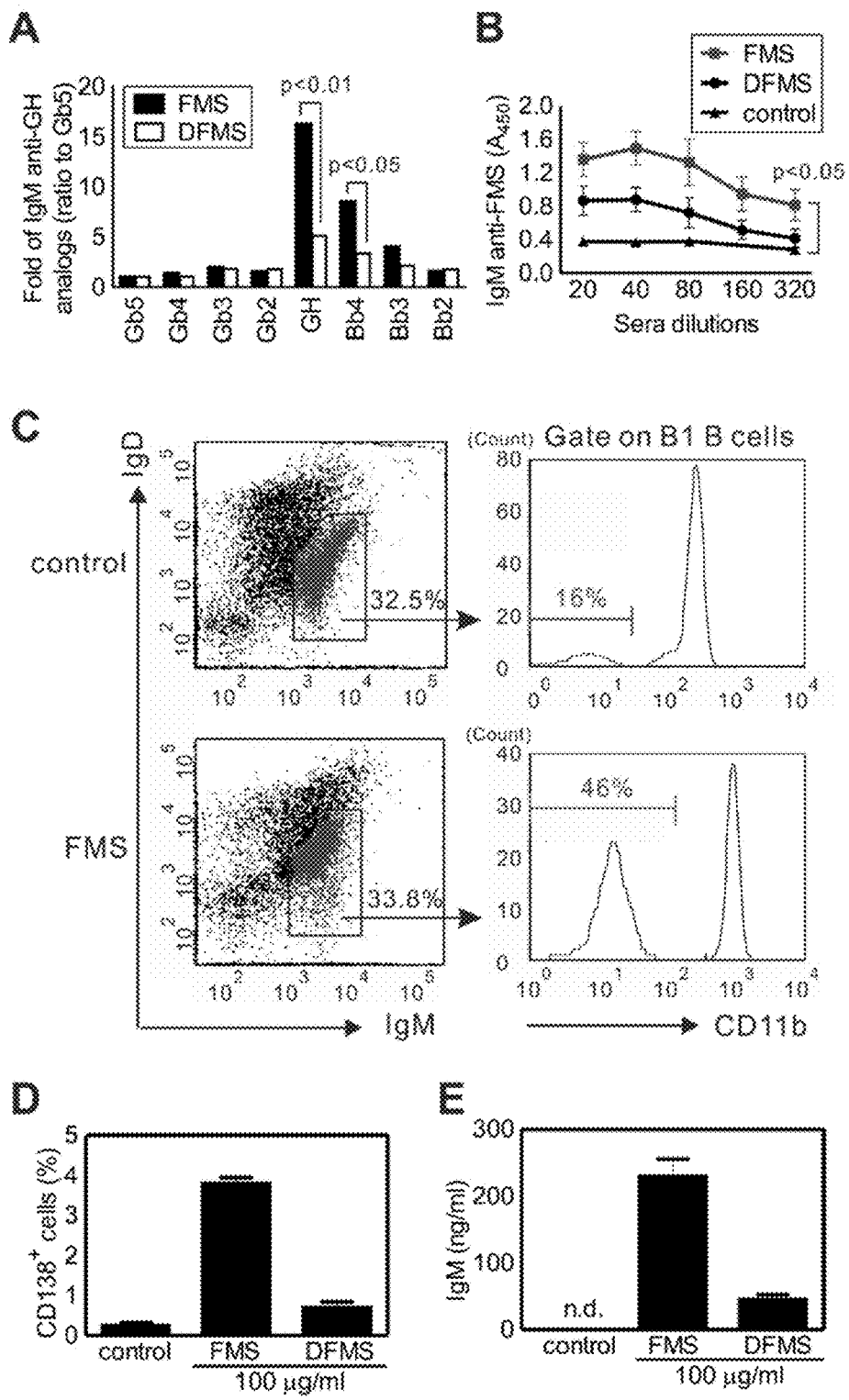
FIG. 4. Correlation between antiglycan IgM production and B1 B cells expansion in the mice immunization with our Reishi polysaccharides. (A and B) Antisera from FMS- and DFMS-treated mice were assessed by Globo H-related printed glycan microarray (A) and FMS-coated ELISA plate (B). (A) Binding of IgM to Globo H (GH) and its truncated forms (tested at 1:100 dilution) was normalized by setting the IgM anti-Gb5 as 1. (B) Binding of IgM to FMS (tested at 1:20 to 1:320 dilution) was measured by detecting the absorbance at 450 nm. (C, D and E) Expansion of peritoneal B1 B cells upon FMS immunization. FACS profiles of B1 B cells represent FMS-treated mice and control. Additional levels of B2 B cell and macrophage are shown in FIG. S4. Numbers (%) indicate the positive cells in each gate (C). FMS induced up-regulation of plasma cell surface marker (CD138) (D) and IgM production (E) in ex vivo B1 B cells culture purified from FMS-treated mice. Means±SD (n=3-5 for each experiment). n.d.=not detectable.

To investigate if the α-fucosyl residues of FMS are correlated with anti-tumor activities, we selectively removed the terminal fucose of FMS by a recombinant □-L-fucosidase from *Bacteroides fragilis*. A modified form of FMS, named as DFMS, was obtained after enzymatic hydrolysis and subsequent purification. The fucose content in DFMS was 50% of that in FMS, as determined by the HPAEC/PAD method. We then compared the anti-tumor efficacy of DFMS and FMS using the preventive immunization plan as mentioned earlier. Both the CDC activity and tumor growth analysis showed that DFMS did not display appreciable inhibition on the survival of LLC1 cells in vitro and in vivo (FIGS. 3F and G), contrary to FMS. Furthermore, there is no statistically significant difference in MCP-1 levels between DFMS-treated mice and the control mice, in contrast to the observed reduction of sera MCP-1 in FMS group (FIG. 3H). These results strongly supported a direct connection between the terminal fucosylation levels of FMS and the anti-tumor efficacy. To validate if the serum antibodies are directly involved in the anti-tumor activity, and to study if the antisera from different treatments have any change in the glycan-binding specificity, the Globo H-related printed glycan microarray was applied. As expected, the serum IgM against Globo H was significantly reduced in the DFMS group ($p<0.01$ versus FMS group), consistent with its distinct anti-tumor effect (FIG. 4A and saccharide structures are shown in FIG. 7). Furthermore, we also confirmed that the FMS-induced antisera to FMS were detectable in the dilution range between 1:20 to 1:320 while the quantities of FMS-binding IgM antibodies were substantially reduced in the DFMS group, as determined by the FMS-coated 96-well plates ($p<0.05$) (FIG. 4B). However, no IgG isotype in response to serological assays was detected in either study group using the same dilution factor. Because the total IgM production of each group (FMS versus DFMS) was similar, the results of these tests demonstrated that terminal fucosyl residues of FMS are critical to its immunogenicity. Although mushroom polysaccharides containing β-glucose and α-mannose have been postulated to have antitumor actions through innate carbohydrate-recognizing receptor interactions (42, 43). Our results highlight the importance of terminal fucose on Reishi polysaccharides in the anti-tumor activities.

Immunization with FMS Stimulates B1 B-Cell Activation

Figure 8:
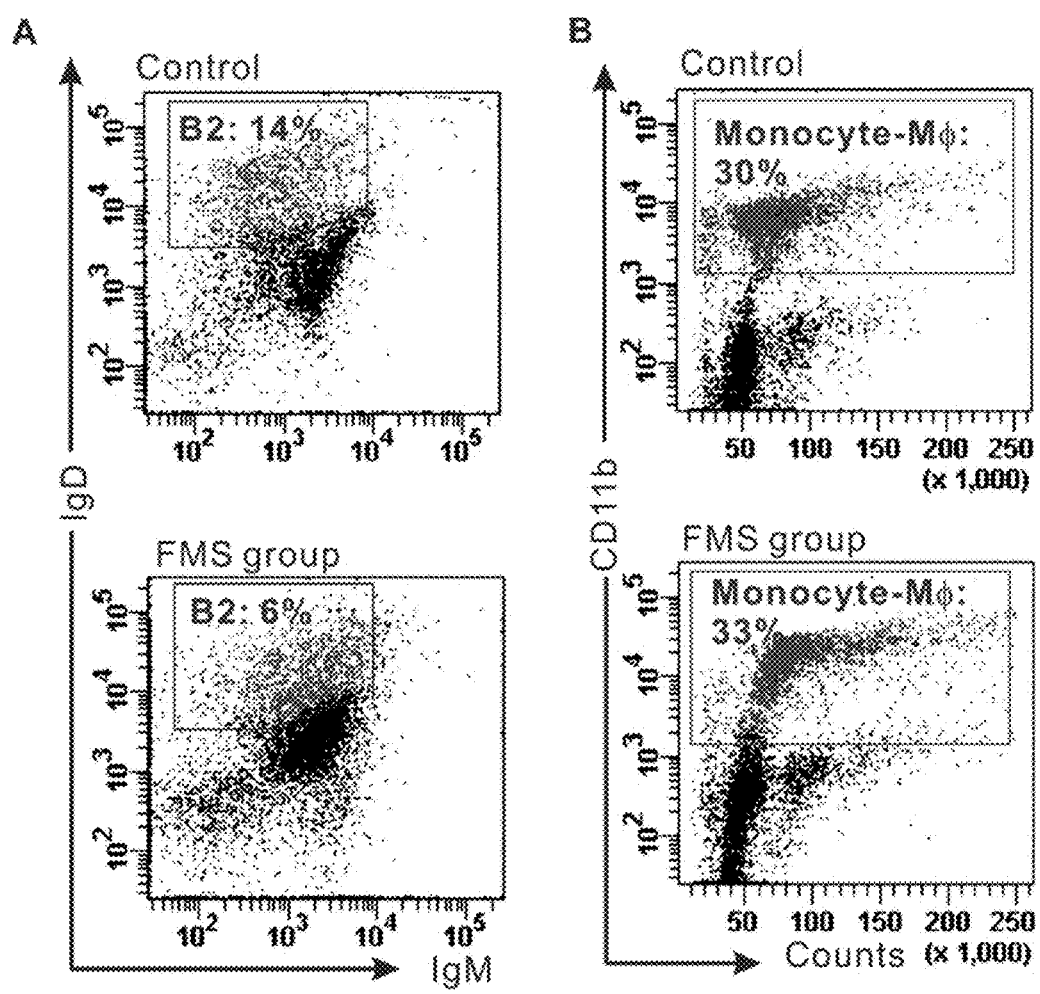
FIG. 8. FACS profiles of cells population in FMS-treated and control mice peritoneal cavities. The positive cells in each gate are shown in numbers (%). There is no significant difference in subpopulation of B2 B cell (A) and macrophage (B) between PBS-treated (control) and FMS-treated mice. n=3~5 for each group.

Most anti-glycan/polysaccharide antibodies belong to the IgM isotype, which is likely produced by a subset of B cells known as B1 B cells (12, 13). Since the majority of B1 B cells reside predominantly in the peritoneal and pleural cavities of mice, we thus investigated if there was any cellular change in the mice peritoneal cavity after one month of FMS treatment. The result is depicted in FIG. 4C (see also FIG. 8). We found that the percentages of B1 B cells) ($IgM^{hi}IgD^{lo}CD11b^{lo}$) in FMS-treated mice dramatically increased (up to 46%) in comparison with the control (only 16%), whereas both B2 B cells ($IgD^{hi}$) and the monocyte-macrophage (Mφ) ($CD11b^{hi}$) populations remained similar to those of the control, as indicated by flow cytometry. To further confirm if the increased levels of peritoneal B1 B cells are directly associated with FMS-specific antibody responses, we purified both B1 B and B2 B cells from the peritoneal cavities of FMS-treated mice and cultured ex vivo in the presence of either FMS or DFMS for 3 days. As expected, the addition of FMS to the culture caused a dramatic increase of B1 B cells that were positive for CD138 expression, a surface marker for plasma cells, whereas only an insignificant amount of CD138$^+$ B1 B cells was detected upon DFMS treatment (FIG. 4D). Additionally, we observed a considerable increase in IgM production after ex vivo culture of B1 B cells with FMS, but not with DFMS treatment (FIG. 4E). However, neither FMS nor DFMS caused any noticeable effect on B2 B-cell activation. Although in vivo integrated immune responses involved in the activation of B1 B cells remain unclear, our data support that the peritoneal B1 B cells play a direct role in responding to FMS as well as TI antigens, resulting in an enhanced level of FMS-specific antibody-secreting cells (plasmablasts) along with increased IgM antibodies.

Identification of Fucosyl Glycan Moieties of FMS by MS-Based Approach

Based on the afore-mentioned sugar composition and linkage analysis, we concluded that FMS, unlike some common glycans, comprises Fuc, Gal, Man and Xyl (Table 3).

TABLE 3

Glycosyl-linkage composition of FMSa and DFMSa

| | | Values (%) [b] | |
|---|---|---|---|
| Alditol | Glycosyl linkage | FMS | DFMS |
| 2,3,4-tri-O—Me-Fuc | t-Fucp | 20 | <10 |
| 3,4-di-O—Me-Fuc | 2-Fucp | <1 | trace |
| 2,3,4-tri-O—Me-Xyl | t-Xylp | 4 | 9.5 |
| 3,4- or 2,3-di-O—Me-Xyl | 2- or 4-Xylp | 14 | 10 |
| 2,3,4,6-tetra-O—Me-Man | t-Manp | 2 | 4.5 |
| 2,4,6-tri-O—Me-Man | 3-Manp | 3 | 7 |
| 2,3,6-tri-O—Me-Man | 4-Manp | 9 | 7 |
| 2,6-di-O—Me-Man | 3,4-Manp | 20 | 24 |
| 2,3,4,6-tetra-O—Me-Gal | t-Galp | <1 | <1 |
| 2,3,4-tri-O—Me-Gal | 6-Galp | 17 | 23 |
| 3,4-di-O—Me-Gal | 2,6-Galp | 8 | 3 | aThe sample was subjected to a sequence of permethylation, hydrolysis, reduction, peracetylation, and the glycosyl linkage was deduced from the GC-MS analysis of the resulting O-methylated alditol acetates.
[b] Value (%) of peak area relative to total peak area were average of duplicated determinations.

Figure 10:
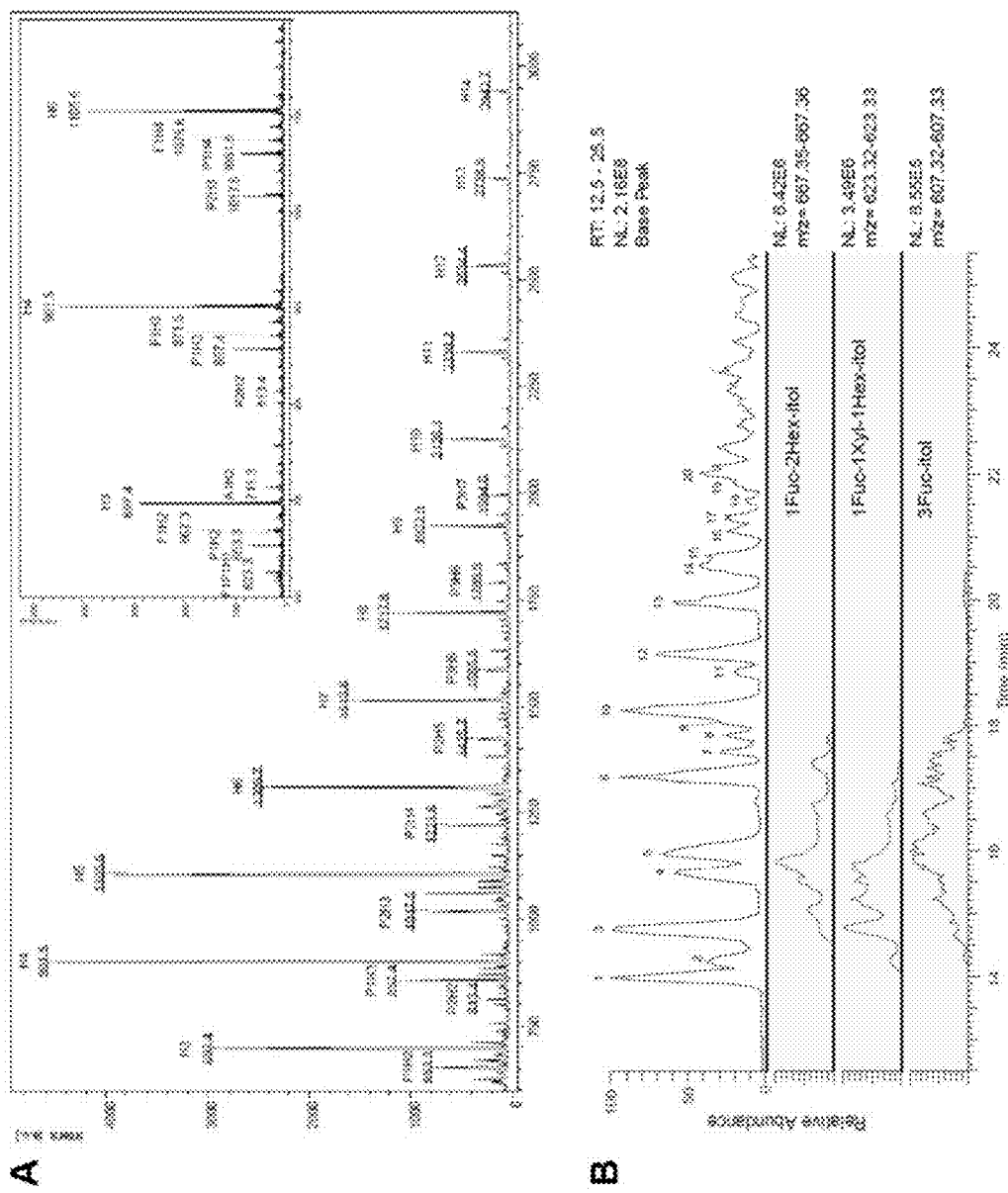

In particular, the sugar analysis supports the presence of a significant amount of terminal fucose residues, which is of immunobiological relevance. Using a competition assay, we found that intact FMS (MW of ~35 kDa) and the small glycan fragments (MW<3 kDa) derived from FMS or algal fucoidan (FMS-H or fucoidan-H, respectively, prepared by partial acid hydrolysis) all served as competitive inhibitors to decrease the interactions of the FMS-induced antisera with Globo H-printed glycan microarray, whereas an intact algal fucoidan (Sigma F-5631) purified from *Fucus vesiculosus* did not (FIG. 9B) (44). The result supports that fucosylated and/or oligofucosylated glycans, which can be released by acid hydrolysis from FMS, are the most promising small immuno-active molecules to be identified as biologics. Inexplicably, a MALDI-MS mapping of the partial hydrolysates failed to detect such convincingly fucosylated fragments among the predominant oligo-hexoses despite the apparent abundance of Fuc in the FMS (FIG. 10A). We therefore conducted the nanoLC-MS/MS analysis of the permethylated oligoglycosyl alditols, taking advantage of the highest sensitivity and selectivity afforded by a Fuc-dependent MS$^n$ data acquisition. In this mode, as many MS$^2$ analyses as possible were initially performed on as many detectable peaks, but only few targeted product ions would be further analyzed. In essence, the MS/MS functions would automatically sieve through hundreds of peaks and focus only on those of interest, which in this case are the minor components carrying terminal Fuc. It is evident from the LC-MS profiles that these fucosylated oligosaccharides were 100-fold less abundant than the Hex-only oligosaccharides, which may constitute the structural backbone of FMS (FIG. 10B). Among the MS$^2$ product ions afforded by fucosylated precursors, the B ions of three distinct terminal fucosylated disaccharide epitopes, namely Fuc-Hex, Fuc-Xyl, and Fuc-Fuc at m/z 415, 371 and 385, respectively, were further isolated for MS$^3$ analysis to confirm their identities and define their linkages. Four selected pairs of MS$^2$/MS$^3$ spectra are depicted in FIG. 11, which are representative of the range of fucosylated epitopes carried by FMS. Through manual interpretation of the fragment ions, it is clear that a terminal Fuc residue can indeed be directly attached to a Hex (Man or Gal), Xyl, or another Fuc, most commonly at the C4 and C2 position in each case, although it is not possible to rule out other co-existing linkages. The Fuc-Hex moiety can be further extended at the reducing end by another Hex or Xyl, whereas a Fuc-Xyl unit can be extended by another Hex. Intriguingly, a stretch of tri-Fuc can also be found, along with alternative isomers in which the Fuc residue is located internally or at the reducing end. These results may explain our observation that the possible molecular basis of the FMS-induced IgM antibodies could cross-react with H-type 3/4 glycans (30, 45-47).

The immunogenic compositions described herein may comprise an adjuvant. An adjuvant is an agent that modifies the immunogenicity of the glycan conjugate in the composition. Adjuvant typically does not elicit immune responses specific to it but enhances immune responses specific to a given immunogenic agent (an antigen). Adjuvant can be inorganic or organic chemical, macromolecule or whole cells of certain killed bacteria which enhance the immune response to a given antigen. In certain embodiments, the adjuvant is a mineral salt/gel, e.g., aluminium hydroxide and aluminium or calcium phosphate gels. In certain embodiments, the adjuvant is an oil-in water and water-in-oil emulsion, amphiphilic molecule and surfactant based formulation, e.g., MF59 (microfluidised detergent stabilised oil-in-water emulsion), QS-21 (purified saponin, which is plant-derived), AS03 (consisting of an oil-in-water emulsion plus alpha-tocopherol), Montanide ISA-51, and Montanide ISA-720. In certain embodiments, the adjuvant is liposome, virosome (unilamellar liposomal vehicles incorporating influenza haemagglutinin), ISCOMS (structured complex of saponins and lipids), and polylactide co-glycolide (PLG), PLG-Dimethylaminoethane-carbamoyl-Cholesterol (PLGA/DC-cholesterol) particles, and Iscomatrix. In certain embodiments, the adjuvant is aicrobial derivative (natural and synthetic), e.g., monophosphoryl lipid A (MPL), Detox (MPL+*M. Phlei* cell wall skeleton), AGP [RC-529] (synthetic acylated monosaccharide), DC_Chol (lipoidal immunostimulators able to self-organise into liposomes), OM-174 (lipid A derivative), CpG motifs (synthetic oligodeoxynucleotides containing immunostimulatory CpG motifs), modified heat labile enterotoxin (LT) and cholera toxin (CT) (genetically modified bacterial toxins that have been genetically modified to provide non-toxic adjuvant effects); synthetic dsRNA, Poly IC:LC (Hiltonol) and Poly I: Poly C12U (Ampligen®). In certain embodiments, the adjuvant is an endogenous human immunostimulator, e.g., hGM-CSF or hIL-12 (cytokines that can be administered either as protein or plasmid encoded), Immudaptin (C3d tandem array). In certain embodiments, the adjuvant is an inert vehicles, e.g., gold particle. In certain embodiments, the adjuvant is an inert polysaccharides, e.g., Advax (delta-inulin), derived from plants (dahlias). In certain embodiments, combination adjuvants or adjuvant systems can used in the immunogenic compositions described herein, for example, combinations of vaccine delivery systems and immunostimulatory agents. Combination adjuvants or adjuvant systems may result in more effective delivery of the immunostimulatory adjuvant as well as the antigen, e.g., AS01 consisting of liposomes, MPL, and QS-21; AS02 consisting of an oil-in-water emulsion plus MPL and QS-21; AS03 consisting of an oil-in-water emulsion plus alpha-tocopherol; AS04 consisting of MPL and aluminum hydroxide; AS15 consisting of liposomes, MPL, QS-21 and a CpG oligodeoxynucleotide; and GLA-SE consisting of a synthetic acylated monosaccharide in a stable oil in-water emulsion.

In some embodiments, the adjuvant used in the immunogenic compositions described herein is selected from C34, 7DW8-5, C17, C23, C30, α-galactoceramide, Aluminum salt, Squalene, MF59, or QS-21 (see U.S. Pat. No. 8,268,969 and U.S. Publication No. 2008-0260774, both of which are incorporated herein by reference).

A variety of means can be used to formulate the compositions of the invention. Techniques for formulation and administration may be found in "Remington: The Science and Practice of Pharmacy," Twentieth Edition, Lippincott Williams & Wilkins, Philadelphia, Pa. (1995). For human or animal administration, preparations should meet sterility, pyrogenicity, and general safety and purity standards comparable to those required by the FDA. Administration of the pharmaceutical formulation can be performed in a variety of ways, as described herein.

The immune composition described herein can be administered parenterally (e.g., intravenous injection, subcutaneous injection or intramuscular injection). Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders and contain 10-95% of the immune composition described herein.

The immune composition is administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art. Suitable regimes for initial administration and booster doses are also variable, but may include an initial administration followed by subsequent administrations. The dosage of the vaccine may also depend on the route of administration and varies according to the size of the host.

The immune composition of this invention can also be used to generate antibodies in animals for production of antibodies, which can be used in both cancer treatment and diagnosis. Methods of making monoclonal and polyclonal antibodies and fragments thereof in animals (e.g., mouse, rabbit, goat, sheep, or horse) are well known in the art. See, for example, Harlow and Lane, (1988) *Antibodies: A Laboratory Manual*, Cold Spring Harbor Laboratory, New York. The term "antibody" includes intact immunoglobulin molecules as well as fragments thereof, such as Fab, F(ab')2, Fv, scFv (single chain antibody), and dAb (domain antibody; Ward, et. al. (1989) *Nature,* 341, 544).

EXAMPLES

The following examples are put forth so as to provide those skilled in the art with a complete invention and description of how to make and use embodiments in accordance with the invention, and are not intended to limit the scope of what the inventors regard as their discovery. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

MBr1, the mouse IgM anti-Globo H mAb, was purchased from Alexis Biochemicals. Fluorochrome-conjugated mAbs against IgD (11-26c.2a), IgM (R6-60.2), CD11b (M1/70) and CD138 (281-2) were purchased from BD Biosciences. DyLight 649-labeled goat anti-mouse IgG and IgM were purchased from Jackson ImmunoResearch Labs. DEAE Sephadex A-50 and Sephadex G-50 gels were purchased from GE healthcare. Biotinylated lectins, *Aleuria aurantia* lectin (AAL), and *Ulex europaeus* agglutinin I (UEA-I), were purchased from Vector Laboratories. PE-labeled streptavidin were purchased from Invitrogen. 4-Nitrophenyl α-L-fucopyranoside, Fucoidan (*Fucus vesiculosus*), commercial solvents and analytical reagents were purchased from Sigma-Aldrich.

Crude Reishi Extract.

Crude Reishi extract (prepared via alkaline extraction (0.1 N NaOH), neutralization and ethanol precipitation) was obtained from Pharmanex Co. (CA, USA). Immobiline DryStrip (pH 3-10 NL (non-linear), 18 cm) and IPG buffer (pH 3-10 NL) were purchased from Amersham Pharmacia Biotech (Uppsala, Sweden). CHAPS, Tris buffer, agarose, iodoacetamide and alpha-cyano-4-hydroxycinnamic acid were from Sigma Co. (St. Louis, Mo., USA); dithioerythritol (DTE) was from Merck Co. (Darmstast, Germany); acrylamide, ammonium persulfate (APS) and TEMED were from Bio-Rad (Hercules, Calif., USA); sodium dodecyl sulfate (SDS) and glycine were from Fluka (Buchs, Switzerland); sequencing grade trypsin was from Promega (Madison, Wis., USA).

Purification of Reishi Extract Fraction 3 (F3).

Crude Reishi extract (prepared via alkaline extraction (0.1 N NaOH), neutralization and ethanol precipitation) was obtained from Pharmanex Co. (CA, USA). Twenty-eight mg of the crude extract were dissolved in 2 mL of Tris buffer (pH 7.0, 0.1 N) and centrifuged to remove the insoluble materials (7 mg). The supernatant was purified by gel filtration chromatography using a Sephacryl S-500 column (100×1.6 cm) with 0.1 N Tris buffer (pH 7.0) as the eluent. The flow rate was set at 0.5 mL/min, and the elute (7.5 mL per tube) was collected. Five fractions were collected (fractions 1-5), each dialyzed to remove excessive salt and lyophilized to give 1.0 mg, 6.2 mg, 5.3 mg, 2.1 mg, and less than 1 mg, respectively. Fractions 1 to Fractions 5 are identifiable as it follows: Fraction 1: 100-130 mL; Fraction 2: 130-155 mL; Fraction 3: 155-205 mL; Fraction 4: 205-220 mL; Fraction 5: 220-255 mL. The main fraction having a light absorbance of about 1.8 at O.D. 625 was designated as Fraction 3.

Fraction 3 (F3 or Reishi F3) is known to be a heterogeneous and high-molecular-weight polysaccharide (>100 kDa) also including a fucose-containing glycoprotein fraction, which comprises terminal fucose residues. The phrase "terminal fucose residues" identifies fucose residues of a chain of sugars located in a region proximate to a free end of a chain of sugars. The fucose-containing glycoprotein fraction of Fraction 3, also includes fucose residues bound with α1,2-fucosidic linkages and α3,4-fucosidic linkages, which may be located terminally, in a region proximate to a free end of a chain of sugars. In further exemplary implementations, the fucose-containing glycoprotein can also comprise of glucose, mannose, N-acetylglucosamine, xylose, and galactose. An amino acid component may also be included, and may comprise modifications that do not adversely alter characteristics of the fucose-containing glycoprotein. Preparation and some uses of Reishi Fraction 3 (F3) are disclosed in U.S. Pat. Nos. 7,560,114, 7,323,176, 7,135,183, 7,947,283 and 7,785,600, which are incorporated herein by reference.

Preparation of Fucose-Enriched F3 Polysaccharide Fraction, FMS

The starting material is a commercial product (called F3, a crude extract fraction of water-soluble and fucose-containing polysaccharides from *Ganoderma lucidum*, Reishi) manufactured by Wyntek Corp. (Taiwan). F3 was dissolved in 50 mM ammonium acetate and the insoluble residue was removed by centrifugation. The supernatant was fractionated by DEAE-Sephadex™ A-50 chromatography to obtain a fraction using 50 mM ammonium acetate as the eluent. After desalting, the fraction was further purified by reversed phase high performance liquid chromatography (RP-HPLC) using a semi-preparative C8 column coupled with an Agilent 1100 series system. All runs required 0.05% trifluoroacetic acid (TFA) as the eluent and the flow-through were collected. The selected fraction was subjected to Sephadex™ G-50 chromatography (1.5×100 cm) using distilled water as eluent. The carbohydrate-containing fractions, detected using the phenol-sulfuric acid method, were lyophilized to give a polysaccharide product designated as FMS (total yield<0.1%). Polysaccharide preparations were monitored routinely by the Limulus Amebocyte Lysate (LAL) test (Associates of Cape Cod Inc.) to ensure absence of endotoxin contamination.

Glycan Binding Analysis of Serum IgM Antibodies

For a comprehensive glycan microarray analysis, the mice were administrated i.p. with test samples (150 mg/kg of body weight per mouse) twice weekly and the sera samples were harvested on Day 14 after first immunization. PBS-treated mice sera served as control group. The glycan-binding profiling of IgM antibodies were investigated on the glycan microarray at Core H of the Consortium for Functional Glycomics (CFG), Emory University School of Medicine, Atlanta, USA. The sera samples were diluted by 1:100 dilution, and screened using version 5.0 of the printed array containing 611 glycans in hexaplicates. The procedures as well as all glycan structures of the referenced CFG numbers are available on the CFG website (www.functionalglycomics.org).

Characterization of FMS.

For molecular weight determination, FMS (2 mg/ml) was subjected to a size exclusion chromatography column (Shodex SB-806M HQ) equipped with an Agilent 1260 Infinity LC system coupled to DAWN Heleos multi-angle light scattering (MALLS) detector (Wyatt Technology Corp.) and Optilab®T-rEX™ refractive index (RI) detector (Wyatt Technology Corp.). Molecular weight was analyzed using an Astra Software (Wyatt Technology Corp.). The major constituent monosaccharides of FMS were determined by High-Performance Anion-Exchange Chromatography with Pulsed Amperometric Detection (HPAEC-PAD) after hydrolysis with 4M TFA at 121° C. for 1 h. A CarboPac™ PA-10 analytical column was coupled to a Dionex ICS-3000 HPAEC-PAD system (Dionex corp.). The separation was performed at an isocratic concentration of 10 mM NaOH (0.25 ml/min) and the column temperature was at ambient temperature. Monosaccharide standards included L-fucose (Fuc), D-arabinose (Ara), D-xylose (Xyl), D-galactose (Gal), D-glucose (Glc), D-mannose (Man), D-galactosamine ($GalNH_2$) and D-glucosamine ($GlcNH_2$). Alternatively, the monosaccharide residues released by acid hydrolysis were also converted into their alditol acetate and analyzed by combined gas chromatography/mass spectrometry (GC/MS). To further determine the glycosidic linkage positions, methylation analysis was performed, in which the partially methylated alditol acetates (PMAAs) of FMS were analyzed by GC/MS using the established method (49).

Hydrolysis Reactions.

For enzymatic hydrolysis of α-linked fucose residues from FMS, a His-tagged recombinant α-L-fucosidase (EC 3.2.1.51 from *Bacteroides fragilis*) was expressed in *E. coli*. The 4-Nitrophenyl α-L-fucopyranoside was used as chromogenic substrate for evaluation of enzyme activity. The release of fucose by the enzymatic reaction of FMS was monitored by HPAEC-PAD. The enzyme to substrate ratio of 1:25 (wt/wt) was used in phosphate buffer (pH 7) and the reaction mixture was incubated at 37° C. for several days. The fucosidase digestion was repeated several times to ensure completeness of fucose cleavage. The reaction was finally terminated by enzyme removal using Ni-NTA® beads (Qiagene) and then boiling at 100° C. for 10 min. The digest was further purified by Sephadex™ G-50 chromatography in distilled water to obtain high-molecular weight fraction, designated as DFMS. To remove endotoxin contamination, DFMS was passed through Cellufine® ET clean beads (Chisso, Corp.) according to the manufacture's specifications and then recovered by lyophilization. For oligosaccharides preparation, polysaccharide sample was dissolved in 0.1M TFA and heated at 100° C. for 60 min. After cooling, mixtures were filtered through a Centricon centrifugal filter device (Millipore). Finally, the filtrate (MW<3 KDa) was collected, lyophilized and reconstituted before assay.

Fucose-Based Nano-LC Tandem MS Analysis.

NanoLC-MS/MS analysis of the permethylated oligoglycosyl alditols were carried out on a homemade nanoLC system comprising a 50 μm×4 cm homemade polystyrene-divinylbenzene (PS-DVB) monolithic trap column and a 20 μm×4 m homemade PS-DVB grafted open tubular analytical column, coupled to Orbitrap Elite (Thermo scientific) MS system. For this nanoLC system, sample was dissolved in 2 μL of 25% (v/v) acetonitrile, injected into the trap column, and then separated in a serially connected analytical column at a constant flow rate of 150 nl/min, with a linear gradient of 5-40% (v/v) acetonitrile (with 0.5 mM sodium acetate additives) in 25 min, then increased to 80% acetonitrile in 5 min and held isocratically for another 10 min. The eluent was interfaced to the nanospray source based on the liquid junction configuration consisted of an uncoated emitter and a high voltage (around 1.7 kV) platinum electrode. For data-dependent acquisition cycle, the full scan MS spectrum (m/z 350-2000) was acquired in the Orbitrap at 120,000 resolution (at m/z 400) with automatic gain control (AGC) target value of $1\times10^6$. Data-dependent CID-MS$^2$ experiments were performed for the ten most intense ions with intensity threshold of 3000 counts. Following product-ion dependent CID-MS$^3$ experiments were carried out with three distinct B fragment ion candidates at m/z 415.19, 371.16 and 385.18, with intensity threshold of 100 counts, within 25 most intense ions in MS$^2$ spectra. The AGC target value and normalized collision energy applied for CID experiments were set as 30,000, 38%, respectively.

Mice Immunization Schedule and the Lung Tumor Model.

Male C57BL/6 mice (5-6 weeks old) were obtained from the National Laboratory Animal Center (Taiwan). All animal experiments were conducted in accordance with the procedures outlined in the Guide for the Care and Use of Laboratory Animals under an animal study proposal approved by the Animal Care and Use Committee of the Academia Sinica. For investigation of anti-tumor activity of F3, the mice were injected subcutaneously (s.c.) in right flank with $1\sim2\times10^5$ syngeneic LLC1 cells suspended in 0.1 ml of PBS. Each group of mice was then treated with indicated dosage of F3 intraperitoneally (i.p.) (24, 52, 120 and 240 mg/kg of body weight per mouse dissolved in PBS) at 2-day intervals. The tumor volume was measured by an electronic caliper along the long axis (a), the short axis (b), and the height (c). Tumor volumes (mm$^3$) were calculated by the formula: a×b×c. When tumors in control mice reached an average size of 200 mm$^3$, the volumes were recorded every 2-3 days and the mice were sacrificed around 21-28 days after tumor inoculation. To study the anti-tumor effects of FMS (150 mg/kg of body weight per mouse dissolved in PBS), two immunization plans were designed to assess both the preventive and therapeutic potentials as shown in FIG. 9A. All experiments contained at least 4-5 mice per group and were repeated at least once. Age-matched mice received the same injection amount of PBS to serve as control group. Differences in tumor volume were assessed for statistical significance using the two-way ANOVA with PRISM software. A p value of 0.05 or less was accepted as significant.

Serological Analysis of Serum Antibodies.

The serum IgM against synthetic glycans were also examined by our fabricated glycan microarray according to the published protocol (50). To determine the total amount of serum IgM by means of enzyme-linked immunosorbent assay (ELISA), test samples were harvested, serially diluted in PBS containing 1% BSA, and placed into 96-well plates coated with anti-mouse IgM (Bethyl Laboratories, Inc.). The following procedures and methods for detecting captured mouse IgM were essentially according to the manufacturer's suggestions (Bethyl Laboratories). To test the serum antibodies reactivity against FMS, the FMS-based ELISA assays using 96-well MaxiSorp™ plates (Nunc) were prepared according to the procedures described previously (51), using TMB as the substrate, then the plates were read with a reader (Molecular Devices) at 450 nm. All data are presented as the mean±standard deviation (SD). The significance of any differences between means was evaluated by unpaired one-tailed Student's t-test. A value of p<0.05 was considered statistically significant.

Analyses with Fucose-Specific Lectins.

The use of amino-reactive glass slides allows covalent attachment of glycans containing terminal amines by forming an amide bond, leading to speculation that FMS (1 mg) and F3 (1 mg) were possibility printed onto N-hydroxysuccinimide (NHS)-activated glass slides according to this microarray fabrication mechanism. For lectin-reactive glycans detection, each biotinylated lectins (1~10 µg/ml) diluted in TBS buffer containing 1% BSA were added to each subarray on the slide. After washing with TBS buffer, the slides were probed with PE-conjugated streptavidin (1:500) and scanned using a Genepix 4000B microarray scanner (Molecular Devices). Image analysis was extracted by using Genepix software (Molecular Devices). The lectin binding intensity for each test sample is shown as the average relative fluorescence intensities (RFUs) from pentaplicates.

Cell Cultures and FACS Analysis.

For Detection of Globo H antigen expression on the cell surface, mouse Lewis lung carcinoma (LLC1) cells and Tissue culture 1 (TC-1) cells were purchased from BCRC (Bioresource Collection and Research Center, Taiwan). About $2\times10^5$ cells were stained with primary mAb MBr1, followed by washing with PBS and then incubation with a DyLight 649-conjugated goat anti-mouse IgM secondary antibody. For identification of cellular changes in the mice peritoneal cavities, peritoneal exudate cells were harvested by lavage with cold PBS and then the cells were concurrently stained with FITC-conjugated anti-IgD, PerCP-conjugated anti-IgM, and APC-conjugated anti-CD11b mAbs. By means of FACSAria Cell Sorter (BD Biosciences), B-1 B cells were obtained by gating the IgM$^{hi}$IgD$^{int}$CD11b$^{hi}$ cells and B-2 B cells were sorted by gating the IgD$^{hi}$IgM$^{int}$CD11b$^{lo}$. Freshly isolated B cells ($2\times10^6$ cells/ml) were cultured in RPMI 1640 medium (Invitrogen) containing 10% heat-inactivated FBS (Hyclone), penicillin/streptomycin (100 units/ml), and 2-mercaptoethanol (50 µM) and treated with FMS or DFMS (100 µg/ml) respectively at the indicated time. All flow cytometric analysis was performed using FACSCanto (BD Biosciences) and results were analyzed by Flow Jo software.

Mouse Cytokine/Chemokine Detection.

Blood from tumor-bearing mice were taken on Day 7$^{th}$ after last FMS immunization and the diluted mouse serum samples were measured by using the Beadlyte mouse 21-plex cytokine/chemokine detection kit (Upstate/Millipore) followed the protocol provided by the manufacturer and read by a Luminex 100 system (Luminex).

CDC Assay.

Globo H-positive and -negative tumor cell lines, LLC1 and TC-1 were selected for the complement-dependent cytotoxicity (CDC) assay. For quantification of CDC activity, we used the CytoTox 96® Non-Radioactive Cytotoxicity Assay kit (Promega), a non-radioactive method for measuring this LDH release in the culture media, according to the manufacturer's instructions. The sera samples were used directly as the source of polyclonal antibodies and complements. Heat-inactivated sera from FMS-treated (HI-antisera) mice were prepared by incubation of the sera at 56° C. for 30 min to determine the complement depletion effect. Briefly, the cells ($5\times10^4$) were suspended in serum-free medium and treated with diluted test sera to make final mice sera concentration at 1, 5, 10 and 20%. After 90 min incubation at 37° C., the supernatant was mixed with the lactose dehydrogenase (LDH) substrate (1:1, vol/vol) and then absorbance data were collected. According to LDH release amount, the percentage of cell lysis (% cytotoxicity) was calculated by using the following formula: $100\times[(A-C)/(B-C)]$, where A represents an absorbance obtained with diluted test sera (experimental LDH release), B represents an absorbance obtained by lysing all of the target cells with the lysis solution (maximum LDH release), and C represents an absorbance obtained with target cells incubated in serum-free medium served as baseline (spontaneous LDH release).
Binding Competition Assay.

To determine the effects of sugar competitors on the interaction between antisera and Globo H, the serological responses (sera tested at 1:100 dilutions) were examined using Globo H-printed glass slide in the presence of sugar competitors (0.05 mg/ml). Beside intact polysaccharides (FMS-I and Fucoidan-I), their degradative oligosaccharide mixtures (FMS-H and Fucoidan-H) were prepared by acid hydrolysis as described previously, and the relative binding affinity of each group were measured in duplicates and normalized for each group as % of binding.

TABLE 4

| REFERENCES |
|---|
| 1. Wasser S P & Weis A L (1999) Therapeutic effects of substances occurring in higher Basidiomycetes mushrooms: a modern perspective. Crit Rev Immunol 19: 65-96. |
| 2. Vickers A (2000) Recent advances: complementary medicine. BMJ 321: 683-686. |
| 3. Hakomori S (2001) Tumor-associated carbohydrate antigens defining tumor malignancy: basis for development of anti-cancer vaccines. Adv Exp Med Biol 491: 369-402. |
| 4. Dube D H & Bertozzi C R (2005) Glycans in cancer and inflammation. Potential for therapeutics and diagnostics. Nat Rev Drug Discov 4: 477-488. |
| 5. Zhu J, et al. (2009) Synthetic carbohydrate-based anticancer vaccines: the Memorial Sloan-Kettering experience. Expert Rev Vaccines 8: 1399-1413. |
| 6. Slovin S F, et al. (2005) Carbohydrate vaccines as immunotherapy for cancer. Immunol Cell Biol 83: 418-428. |
| 7. Astronomo R D & Burton D R (2010) Carbohydrate vaccines: developing sweet solutions to sticky situations? Nat Rev Drug Discov 9: 308-324. |
| 8. Gilewski T, et al. (2001) Immunization of metastatic breast cancer patients with a fully synthetic globo H conjugate: a phase I trial. Proc Natl Acad Sci USA 98: 3270-3275. |
| 9. Huang Y L, et al. (2013) Carbohydrate-based vaccines with a glycolipid adjuvant for breast cancer. Proc Natl Acad Sci USA 110: 2517-2522. |
| 10. Siber G R (1994) Pneumococcal disease: prospects for a new generation of vaccines. Science 265: 1385-1387. |
| 11. Lesinski G B & Westerink M A (2001) Vaccines against polysaccharide antigens. Curr Drug Targets Infect Disord 1: 325-334. |
| 12. Foote J B & Kearney J F (2009) Generation of B cell memory to the bacterial polysaccharide alpha-1,3 dextran. J Immunol 183: 6359-6368. |
| 13. Martin F, et al. (2001) Marginal zone and B1 B cells unite in the early response against T-independent blood-borne particulate antigens. Immunity 14: 617-629. |
| 14. Alugupalli K R, et al. (2004) B1b lymphocytes confer T cell-independent long-lasting immunity. Immunity 21: 379-390. |
| 15. Wang Y Y, et al. (2002) Studies on the immuno-modulating and antitumor activities of Ganoderma lucidum (Reishi) polysaccharides: functional and proteomic analyses of a fucose-containing glycoprotein fraction responsible for the activities. Bioorg Med Chem 10: 1057-1062. |
| 16. Lin K I, et al. (2006) Reishi polysaccharides induce immunoglobulin production through the TLR4/TLR2-mediated induction of transcription factor Blimp-1. J Biol Chem 281: 24111-24123. |
| 17. Chen W Y, et al. (2010) Effect of Reishi polysaccharides on human stem/progenitor cells. Bioorg Med Chem 18: 8583-8591. |
| 18. Hua K F, et al. (2007) Ganoderma lucidum polysaccharides enhance CD14 endocytosis of LPS and promote TLR4 signal transduction of cytokine expression. J Cell Physiol 212: 537-550. |
| 19. Chen H S, et al. (2004) Studies on the immuno-modulating and anti-tumor activities of Ganoderma lucidum (Reishi) polysaccharides. Bioorg Med Chem 12(21): 5595-5601. |
| 20. Hsu T L, et al. (2009) Profiling carbohydrate-receptor interaction with recombinant innate immunity receptor-Fc fusion proteins. J Biol Chem 284: 34479-34489. |
| 21. Lai C Y, et al. (2010) Immunomodulatory and adjuvant activities of a polysaccharide extract of Ganoderma lucidum in vivo and in vitro. Vaccine 28: 4945-4954. |
| 22. Gao Y, et al. (2005) Antitumor activity and underlying mechanisms of ganopoly, the refined polysaccharides extracted from Ganoderma lucidum, in mice. Immunol Invest 34: 171-198. |
| 23. Lu H, et al. (2003) A water-soluble extract from cultured medium of Ganoderma lucidum (Rei-shi) mycelia suppresses azoxymethane-induction of colon cancers in male F344 rats. Oncol Rep 10(2): 375-379. |
| 24. Wang P Y, et al. (2012) Antitumor and Immunomodulatory Effects of Polysaccharides from Broken-Spore of Ganoderma lucidum. Front Pharmacol 3: 135. |
| 25. Cao Q Z & Lin Z B (2004) Antitumor and anti-angiogenic activity of Ganoderma lucidum polysaccharides peptide. Acta Pharmacol Sin 25: 833-838. |
| 26. Menard S, et al. (1983) Generation of monoclonal antibodies reacting with normal and cancer cells of human breast. Cancer Res 43: 1295-1300. |
| 27. Bremer E G, et al. (1984) Characterization of a glycosphingolipid antigen defined by the monoclonal antibody MBr1 expressed in normal and neoplastic epithelial cells of human mammary gland. J Biol Chem 259: 14773-14777. |
| 28. Slovin S F, et al. (1999) Carbohydrate vaccines in cancer: immunogenicity of a fully synthetic globo H hexasaccharide conjugate in man. Proc Natl Acad Sci USA 96: 5710-5715. |
| 29. Ye L, et al. (2008) Purification, NMR study and immunostimulating property of a fucogalactan from the fruiting bodies of Ganoderma lucidum. Planta Med 74(14): 1730-1734. |
| 30. Alquini G, et al. (2004) Polysaccharides from the fruit bodies of the basidiomycete Laetiporus sulphureus (Bull.: Fr.) Murr. FEMS Microbiol Lett 230: 47-52. |
| 31. Usui T, et al. (1981) Investigation of the heterogeneity of heterogalactan from the fruit bodies of Fomitopsis pinicola, by employing concanavalin A-Sepharose affinity chromatography. J Biochem 89(4): 1029-1037. |

TABLE 4-continued

REFERENCES

32. Hakomori S (2003) Structure, organization, and function of glycosphingolipids in membrane. Curr Opin Hematol 10: 16-24.
33. Clausen H, et al. (1985) Repetitive A epitope (type 3 chain A) defined by blood group A1-specific monoclonal antibody TH-1: chemical basis of qualitative A1 and A2 distinction. Proc Natl Acad Sci USA 82: 1199-1203.
34. Clausen H, et al. (1986) Novel blood group H glycolipid antigens exclusively expressed in blood group A and AB erythrocytes (type 3 chain H). II. Differential conversion of different H substrates by A1 and A2 enzymes, and type 3 chain H expression in relation to secretor status. J Biol Chem 261: 1388-1392.
35. Cui Y, et al. (1993) Human cervical epidermal carcinoma-associated intracellular localization of glycosphingolipid with blood group A type 3 chain. Jpn J Cancer Res 84: 664-672.
36. Kurimoto S, et al. (1995) Detection of a glycosphingolipid antigen in bladder cancer cells with monoclonal antibody MRG-1. Histochem J 27: 247-252.
37. Fridlender Z G, et al. (2011) Monocyte chemoattractant protein-1 blockade inhibits lung cancer tumor growth by altering macrophage phenotype and activating CD8+ cells. Am J Respir Cell Mol Biol 44: 230-237.
38. Stathopoulos G T, et al. (2008) A central role for tumor-derived monocyte chemoattractant protein-1 in malignant pleural effusion. J Natl Cancer Inst 100: 1464-1476.
39. Wang C C, et al. (2008) Glycan microarray of Globo H and related structures for quantitative analysis of breast cancer. Proc Natl Acad Sci USA 105: 11661-11666.
40. Baldus S E, et al. (1996) Characterization of the binding specificity of *Anguilla anguilla* agglutinin (AAA) in comparison to *Ulex europaeus* agglutinin I (UEA-I). Glycoconj J 13: 585-590.
41. Mollicone R, et al. (1996) Recognition of the blood group H type 2 trisaccharide epitope by 28 monoclonal antibodies and three lectins. Glycoconj J 13: 263-271.
42. Lombard Y, et al. (1994) A new method for studying the binding and ingestion of zymosan particles by macrophages. J Immunol Methods 174: 155-165.
43. Wasser S P (2002) Medicinal mushrooms as a source of antitumor and immunomodulating polysaccharides. Appl Microbiol Biotechnol 60: 258-274.
44. Bilan M I, et al. (2002) Structure of a fucoidan from the brown seaweed *Fucus evanescens* C. Ag. Carbohydr Res 337: 719-730.
45. Miyazaki T & Nishijima M (1981) Studies on fungal polysaccharides. XXVII. Structural examination of a water-soluble, antitumor polysaccharide of *Ganoderma lucidum*. Chem Pharm Bull (Tokyo) 29: 3611-3616.
46. Ye L, et al. (2008) Structural elucidation of the polysaccharide moiety of a glycopeptide (GLPCW-II) from *Ganoderma lucidum* fruiting bodies. Carbohydr Res 343: 746-752.
47. Axelsson K, et al. (1971) Polysaccharides elaborated by *Fomes annosus* (Fr.) Cooke. II. Neutral polysaccharides from the fruit bodies. Isolation and purification of a fucoxylomannan by precipitation with the H-agglutinin from eel-serum. Acta Chem Scand 25: 3645-3650.
48. Gao Y, et al. (2005) Effects of water-soluble *Ganoderma lucidum* polysaccharides on the immune functions of patients with advanced lung cancer. J Med Food 8: 159-168.
49. Hsieh Y S, et al. (2008) Structure and bioactivity of the polysaccharides in medicinal plant Dendrobium huoshanense. *Bioorg Med Chem* 16: 6054-6068.
50. Huang Y L, et al. (2013) Carbohydrate-based vaccines with a glycolipid adjuvant for breast cancer. *Proc Natl Acad Sci USA* 110: 2517-2522.
51. Hsu T L, et al. (2009) Profiling carbohydrate-receptor interaction with recombinant innate immunity receptor-Fc fusion proteins. *J Biol Chem* 284: 34479-34489.

All publications, patents and patent applications cited in this specification are herein incorporated by reference as if each individual publication or patent application were specifically and individually indicated to be incorporated by reference. Citation herein of a publication, patent, or published patent application is not an admission that the publication, patent, or published patent application is prior art.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claim.

What is claimed is:

1. An immunogenic composition, consisting of:
    a fucose-enriched Reishi polysaccharide fraction (FMS) of average molecular weight 35 kDa, wherein the FMS is isolated by size-exclusion chromatography from Reishi F3, and wherein the FMS comprises polysaccharides having primarily a backbone selected from 1,4-mannan and 1,6-α-galactan, wherein the backbone is linked to a terminal fucose-containing side-chain; and
    an adjuvant, wherein the adjuvant is a glycolipid.

2. The immunogenic composition of claim 1, wherein the backbone is linked to a terminal fucose-containing side-chain through one or more linkages selected from the group consisting of Fucα1-2Gal, Fucα1-3/4Man, Fucα1-4Xyl and Fucα1-2Fuc.

3. The immunogenic composition of claim 1, wherein the FMS comprises primarily of fucose, xylose, galactose and mannose.

4. The immunogenic composition of claim 1, wherein the FMS comprises glucose, glucosamine and galactosamine.

5. The immunogenic composition of claim 1, wherein the adjuvant is a synthetic analog of α-GalCer selected from the group consisting of: (7DW8-5) and (C34)

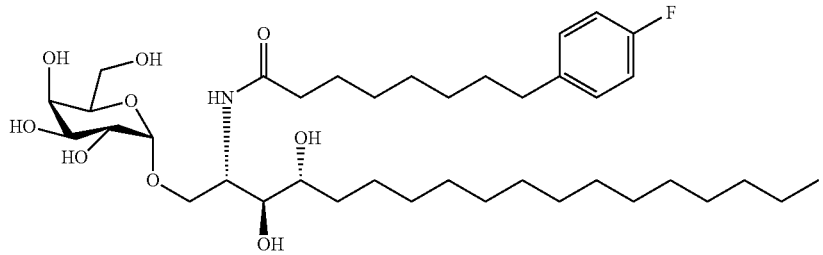

7DW8-5

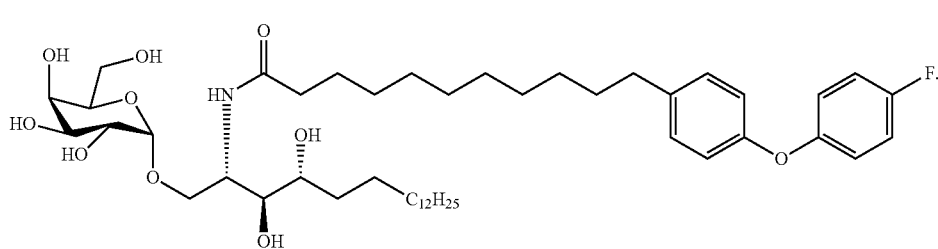

C34

6. The immunogenic composition of claim 1, wherein administration of the composition to a mammal induces IgG antibodies.

7. The immunogenic composition of claim 1, wherein administration of the composition to a mammal induces IgM antibodies.

8. The immunogenic composition of claim 1, wherein the composition induces antibodies that specifically bind to at least one of the tumor-associated antigens selected from the group consisting of Globo H, Gb3 (Galα1-4Galβ1-4Glc), Gb4 (GalNAcβ1-3Galα1-4Galβ1-4Glc), stage-specific embryonic antigen-3 (SSEA-3; Gb-5; or Galβ1-3Gal-NAcβ1-3Galα1-4Galβ1-4Glc) and SSEA-4 (Neu5Acα2-3Galβ1-3GalNAcβ1-3Galα1-4Galβ1-4Glc).

9. The immunogenic composition of claim 1, wherein the composition induces antibodies that specifically bind to a glycan antigen comprising a common structure: Fucα1-2Galβ1-3GalNAc-R in the non-reducing termini.

10. The immunogenic composition of claim 9, wherein the composition induces antibodies that specifically bind to an antigen comprising an additional disaccharide extension in the reducing end of Fucα1-2Galβ1-3GalNAc-R, wherein the disaccharide moiety is selected from the group consisting of: Fucα1-2Gal-R; Fucα1-3/4Man-R; Fucα1-4Xyl-R and Fucα1-2Fuc-R.

11. The immunogenic composition of claim 10, wherein the composition induces antibodies that specifically bind to α-L-fucose-specific lectin or UEA-I (*Ulex europaeus* agglutinin-I).

12. The immunogenic composition of claim 1, wherein the composition induces antibodies that specifically bind to a glycan antigen comprising a blood group ABH determinant.

13. The immunogenic composition of claim 1, wherein the composition induces antibodies that trigger complement-dependent cytotoxicity (CDC) in a cancer cell.

14. The immunogenic composition of claim 13, wherein the CDC activity is sufficient to reduce tumor size in a lung cancer.

15. The immunogenic composition of claim 13, wherein administration of the composition results in decrease of serum levels of monocyte chemoattractant protein-1 (MCP-1).

16. A cancer vaccine comprising the immunogenic composition of claim 1; and
   a pharmaceutically acceptable excipient,
   wherein pretreatment with the composition causes greater reduction of tumor volume in non-small-cell lung cancer (NSCLC) as compared to treatment after induction of the cancer.

17. The cancer vaccine of claim 16, wherein levels of monocyte chemoattractant protein-1 (MCP-1), chemokine (C-X-C motif) ligand 1 (CXCL1/KC) and granulocyte colony-stimulating factor (G-CSF) are decreased in mammals pretreated with the composition.

18. The cancer vaccine of claim 16, wherein the adjuvant is a synthetic analog of α-GalCer selected from the group consisting of: (7DW8-5) and (C34)

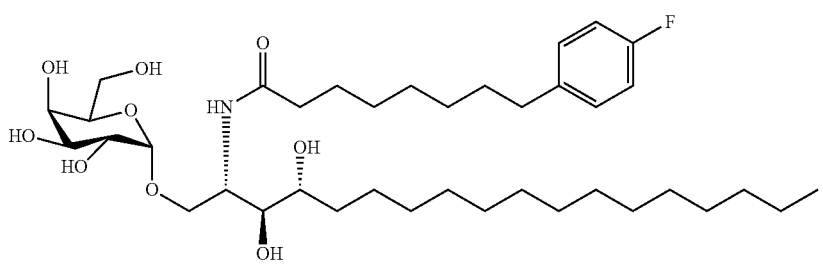

7DW8-5

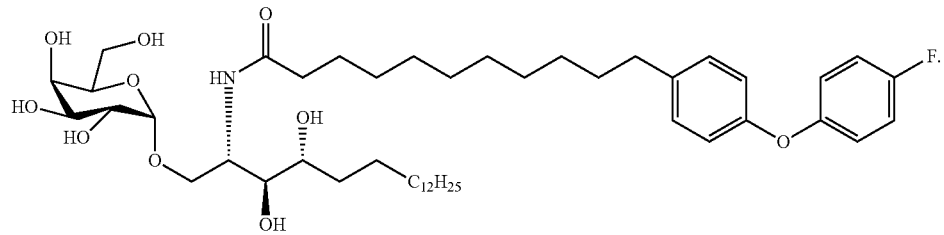

C34

19. The cancer vaccine of claim 16, wherein administration of the composition to a mammal induces IgG antibodies.

20. The cancer vaccine of claim 16, wherein administration of the composition to a mammal induces IgM antibodies.

21. A therapeutic against cancer cells, the therapeutic consisting of:
   a fucose-enriched Reishi polysaccharide fraction (FMS) of average molecular weight 35 kDa, wherein the FMS is isolated by size-exclusion chromatography from Reishi F3, and wherein the FMS comprises polysaccharides having primarily a backbone selected from 1,4-mannan and 1,6-α-galactan, wherein the backbone is linked to a terminal fucose-containing side-chain; and
   an adjuvant, wherein the adjuvant is a glycolipid.

22. The therapeutic of claim 21, wherein administration of the therapeutic to a subject induces production of antibodies that recognize Globo H or a GloboH-related glycan antigen expressed on a cancer cell.

23. The therapeutic of claim 22, wherein the Globo H or a GloboH-related glycan antigen is selected from the group consisting of Globo H, Gb3 (Galα1-4Galβ1-4Glc), Gb4 (GalNAcβ1-3Galα1-4Galβ1-4Glc), stage-specific embryonic antigen-3 (SSEA-3; Gb-5; or Galβ1-3GalNAcβ1-3Galα1-4Galβ1-4Glc) and SSEA-4 (Neu5Acα2-3Galβ1-3GalNAcβ1-3Galα1-4Galβ1-4Glc).

24. The therapeutic of claim 21, wherein the cancer cells are non-small-cell lung cancer (NSCLC) cells.

25. The therapeutic of claim 21, wherein the backbone is linked to a terminal fucose-containing side-chain through one or more linkages selected from the group consisting of Fucα1-2Gal, Fucα1-3/4Man, Fucα1-4Xyl and Fucα1-2Fuc.

26. The therapeutic of claim 21, wherein the FMS comprises primarily of fucose, xylose, galactose and mannose.

27. The therapeutic of claim 21, wherein the FMS comprises glucose, glucosamine and galactosamine.

28. A method of reducing severity and/or frequency of symptoms of a tumor, wherein the adjuvant is a glycolipid, the method comprising:
   1 administering to a subject in need thereof an immunogenic composition consisting of: a fucose-enriched Reishi polysaccharide fraction (FMS) of average molecular weight 35 kDa, wherein the FMS is isolated by size-exclusion chromatography from Reishi F3, and wherein the FMS comprises polysaccharides having primarily a backbone selected from 1,4-mannan and 1,6-α-galactan, wherein the backbone is linked to a terminal fucose-containing side-chain; and an adjuvant, in an amount effective to
   induce an immune response that causes inhibition of tumor growth, wherein the adjuvant is glycolipid.

29. The method of claim 28, wherein the backbone is linked to a terminal fucose-containing side-chain through one or more linkages selected from the group consisting of Fucα1-2Gal, Fucα1-3/4Man, Fucα1-4Xyl and Fucα1-2Fuc.

30. The method of claim 28, wherein the FMS comprises primarily of fucose, xylose, galactose and mannose.

31. The method of claim 30, wherein the adjuvant is a synthetic analog of α-GalCer selected from the group consisting of: 7DW8-5 and C34

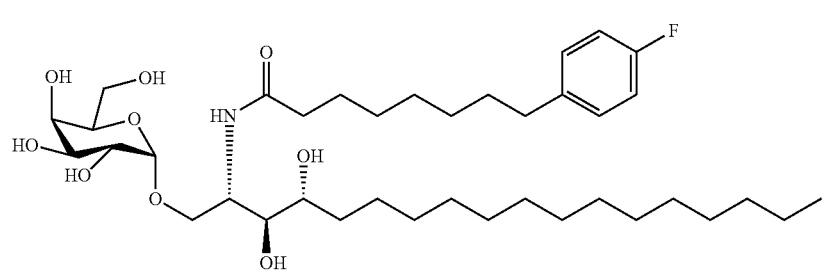

(7DW8-5)

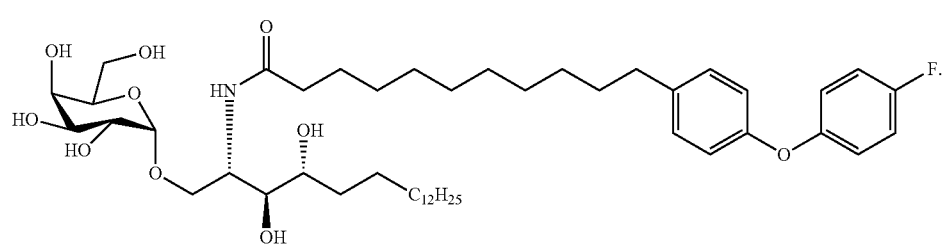

(C34)

32. The method of claim 28, wherein the composition is administered in an amount effective to induce IgG antibodies.

33. The method of claim 28, wherein the composition is administered in an amount effective to induce IgM antibodies.

34. The method of claim 28, wherein the composition is administered in an amount effective to induce antibodies that specifically binds to at least one of the tumor-associated antigens selected from the group consisting of Globo H, Gb3 (Galα1-4Galβ1-4Glc), Gb4 (GalNAcβ1-3Galα1-4Galβ1-4Glc), stage-specific embryonic antigen-3 (SSEA-3; Gb-5; or Galβ1-3GalNAcβ1-3Galα1-4Galβ1-4Glc) and SSEA-4 (Neu5Acα2-3Galβ1-3GalNAcβ1-3Galα1-4Galβ1-4Glc).

35. The method of claim 28, wherein the composition is administered in an amount effective to induce antibodies that specifically bind to a glycan antigen comprising a common structure: Fucα1-2Galβ1-3GalNAc-R in the non-reducing termini.

36. The method of claim 35, wherein the composition is administered in an amount effective to induce antibodies that specifically bind to an antigen comprising an additional disaccharide extension in the reducing end of Fucα1-2Galβ1-3GalNAc-R, wherein the disaccharide moiety is selected from the group consisting of: Fucα1-2Gal-R; Fucα1-3/4Man-R; Fucα1-4Xyl-R and Fucα1-2Fuc-R.

37. The immunogenic composition of claim 1, wherein the FMS comprises primarily of fucose, xylose, galactose and mannose in the ratio of 2:1.5:2.5:3.5 as determined by a high-performance anion-exchange chromatography with pulsed amperometric detection (HPAEC-PAD) method.

38. The therapeutic of claim 21, wherein the FMS comprises primarily of fucose, xylose, galactose and mannose in the ratio of 2:1.5:2.5:3.5 as determined by a high-performance anion-exchange chromatography with pulsed amperometric detection (HPAEC-PAD) method.

39. The method of claim 28, wherein the FMS comprises primarily of fucose, xylose, galactose and mannose in the ratio of 2:1.5:2.5:3.5 as determined by a high-performance anion-exchange chromatography with pulsed amperometric detection (HPAEC-PAD) method.

* * * * *